United States Patent
Luly et al.

(12) 
(10) Patent No.: US 6,288,083 B1
(45) Date of Patent: Sep. 11, 2001

(54) CHEMOKINE RECEPTOR ANTAGONISTS AND METHODS OF USE THEREFOR

(75) Inventors: Jay R. Luly, Wellesley, MA (US); Yoshisuke Nakasato; Etsuo Ohshima, both of Sunto-gun (JP)

(73) Assignees: Millennium Pharmaceuticals, Inc., Cambridge, MA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/148,236

(22) Filed: Sep. 4, 1998

(51) Int. Cl.$^7$ ................. A61K 31/4545; C07D 401/06; C07D 401/10; C07D 401/14; A61P 29/00; A61P 37/08

(52) U.S. Cl. ................. 514/318; 514/230.5; 514/235.5; 514/255.05; 514/252.03; 514/257; 514/259; 514/278; 544/71; 544/231; 544/129; 544/238; 544/333; 544/360; 544/405; 546/16; 546/17; 546/18; 546/20; 546/194

(58) Field of Search ................. 546/17, 18, 20, 546/16, 194; 544/71, 231, 129; 514/230.5, 259, 278, 318, 235.5

(56) References Cited

U.S. PATENT DOCUMENTS

| | | | |
|---|---|---|---|
| 2,712,020 | 6/1955 | Adamson | 260/294.8 |
| 3,238,216 | 3/1966 | Janssen | 260/293.4 |
| 3,770,729 | 11/1973 | Nakanishi et al. | 260/240 |
| 3,940,386 | 2/1976 | Szabo et al. | . |
| 4,206,213 | 6/1980 | Kleeman et al. | 424/250 |
| 4,250,176 | 2/1981 | Vandenberk et al. | 424/250 |
| 4,931,450 | 6/1990 | Sonnewald | 514/326 |
| 5,010,090 | 4/1991 | Gronvald et al. | 514/326 |
| 5,801,175 | 9/1998 | Afonso et al. | 514/254 |
| 6,136,827 | 10/2000 | Caldwell et al. | 514/329 |
| 6,140,349 | 10/2000 | Caldwell et al. | 514/326 |

FOREIGN PATENT DOCUMENTS

| | | |
|---|---|---|
| 240 698 | 6/1987 | (CS) . |
| 80449 | 9/1969 | (DD) . |
| 2 162 802 | 9/1972 | (DE) . |
| 24 31 178 A1 | 1/1975 | (DE) . |
| 28 00 535 A1 | 7/1978 | (DE) . |
| 0029420 | 5/1981 | (EP) . |
| 1 462 206 | 12/1966 | (FR) . |
| 05043548 | 2/1993 | (JP) . |
| WO 90/13539 | 11/1990 | (WO) . |
| WO 96/31469 | 10/1996 | (WO) . |
| WO 96/31470 | 10/1996 | (WO) . |
| WO 96/31498 | 10/1996 | (WO) . |
| WO 97/09983 | 3/1997 | (WO) . |
| WO97/24325 | 7/1997 | (WO) . |
| WO 97/44329 | 11/1997 | (WO) . |
| WO 98/04554 | 2/1998 | (WO) . |
| WO 98/11092 | 3/1998 | (WO) . |
| WO 98/11093 | 3/1998 | (WO) . |
| WO 98/11096 | 3/1998 | (WO) . |
| WO 98/11097 | 3/1998 | (WO) . |
| WO 98/11098 | 3/1998 | (WO) . |
| WO 98/11099 | 3/1998 | (WO) . |
| WO 98/11106 | 3/1998 | (WO) . |
| WO 98/25604 | 6/1998 | (WO) . |
| WO 98/25605 | 6/1998 | (WO) . |
| WO 98/25617 | 6/1998 | (WO) . |
| WO 98/27815 | 7/1998 | (WO) . |
| WO 00/14086 | 3/2000 | (WO) . |

OTHER PUBLICATIONS

Adamson DW et al. J. Chem. Soc. pp. 312–324, 1958.*
XP–002103024, Database WPI, Section Ch, Week 8128, Derwent Publications Ltd., London, GB; Class B03, AN 81–50785D and JP 56 061373 A (Hokuriku Pharm Co., Ltd.) May 26, 1981.
Sato, M. et al., "Psychotropic Agents I. Synthesis of 1–Pyridinyl–1–Butanones, 1–Indolyl–1–Butanones and the Related Compounds," *Chem. Pharm. Bull.*, 26(11): 3296–3305 (1978).
Ng, H. P et al., Chemical Abstracts, 132: 8707 (1999).
March, Jerry, *Advanced Organic Chemistry*, (John Wiley & Sons, Inc.), pp. 136–139 (1985).
Davis, M. A. et al., "New Psychotropic Agents.VIII Analogs of Amitriptyline Containing Normeperidine Group," *New Psychotropic Agents VIII*. pp. 627–635 (Jul. 1967).
Helwig, H., et al., "Helwig/Otto Arzneimittal", *Arzneimittal*, 1:4–1 through 4–24, 8th Ed., (1992).
Sindelar, Karel, et al., "Potential Antidiarrheal Agents:1–(11–Cyano–6,11–Dihydrodibenzo[b,e] Thiepin–11YL–Alklyl)– and 1–(10–Cyano–10,11–Dihydrobibenzo[b,f]Thiepin–10–YL–Alkyl)–4–Substituted Piperidines," *Collection Czechoslovak Chem. Commun.*, 50:1089–1096 (1985).
Hesselgesser, Joseph, et al., "Identification and Characterization of Small Molecule Functional Antagonists of the CCR1 Chemokine Receptor", *The Journal of Biological Chemistry*, 273(25) :15687–15692 (Jun. 19, 1998).
Chemical Abstracts, 121(3) :35275n (1994).
Sindelar, Karel, et al., "Antihistamine Substances: Tricyclic Analogues of N–(4,4–Diphenyl–3Butene–1YL)Nipecotic Acid and Some Related Compounds," *Collection Czechoslovak Chem. Commun.*, 59:667–674 (1994).*

(List continued on next page.)

Primary Examiner—Evelyn Mei Huang
(74) Attorney, Agent, or Firm—Hamilton, Brook, Smith & Reynolds, P.C.

(57) ABSTRACT

Disclosed are novel compounds and a method of treating a disease associated with aberrant leukocyte recruitment and/or activation. The method comprises administering to a subject in need an effective amount of a compound represented by the following structural formula:

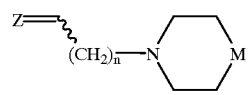

and physiologically acceptable salts thereof.

44 Claims, 12 Drawing Sheets

OTHER PUBLICATIONS

Ali, Fadia E., et al., "Orally Active and Potent Inhibitors of γ–Aminobutyric Acid Uptake," *J. Med. Chem.* 28:653–660 (1985).*

Sindelar, Karel, et al., "Potential Antihistaminics: Tricyclic Carboxylic Acids Derived from 6,11–Dihydrodibenzo[b,e] Thiepine and 4,9 Dihydrothieno[2,3–c]–2–Benzothiepine," *Collection Czechoslovak Chem. Commun.* 56:2482–2493 (1991).*

Polivka, Zdenek, et al., "Heterocyclic Ethers Derived from 6,11–Dihydrodibenzo–[b,e]Thiepin–11–OLS and 4,9–Dihydrothieno[2,3–c]–2–Benzothiepin–4–OL; A New Series of Potential Antidepressants and Antihistamine Agents," *Collection Czechoslovak Chem. Commun.* 51:2034–2049 (1986).*

Polivka, Zdenek, et al., "Antiaminic Agents Derived from Thieno[2,3–c]–2–Benzothiepin: 4–(1–Methyl–4–Piperidylidene)–4,9–Dihydrothieno[2, 3–c]– 2–Benzothiepin and Some Related Compounds," *Collection Czechoslovak Chem. Commun.* 48:623–641 (1983).*

Rajsner, M., et al., "Neurotrope Und Psychotrope Substanzen XV. 4,9–Dihydrothieno[2,3–b]Benzo[e]Thiepin–Derivate," *Collection Czechoslovak Chem. Commun.* 32:2854–2866 (1967).*

Rajsner, M., et al., "Neurotropic and Psychotropic Comounds.XXXI Chemistry and Pharmacology of 11–(3–Dimethylaminopropylidene)–2–Mehtyl–6, 11–Dihydrodibenzo[b,e] Thiepin and of Some Analogues," *Collection Czechoslovak Chem. Commun.* 34:1015–1024 (1969).*

Bengtsson, B.O. et al., Chemical Abstracts, 117:143039 (1992).

Hoegberg, T. and Ulff, B., Chemical Abstracts, 101:190727 (1984).

\* cited by examiner

Example 81

Example 82

Example 83

Example 84

Example 85

Example 86

Example 87

Example 88

Example 89

Example 90

CHEMOKINE RECEPTOR ANTAGONISTS AND METHODS OF USE THEREFOR

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C-X-C chemokines (α-chemokines), and the C-C chemokines (β-chemokines), in which the first two conserved cysteines are separated by an intervening residue, or adjacent respectively (Baggiolini, M. and Dahinden, C. A., *Immunology Today*, 15:127–133 (1994)).

The C-X-C chemokines include a number of potent chemoattractants and activators of neutrophils, such as interleukin 8 (IL-8), PF4 and neutrophil-activating peptide-2 (NAP-2). The C-C chemokines include RANTES (Regulated on Activation, Normal T Expressed and Secreted), the macrophage inflammatory proteins 1α and 1β (MIP-1α and MIP-1β), eotaxin and human monocyte chemotactic proteins 1-3 (MCP-1, MCP-2, MCP-3), which have been characterized as chemoattractants and activators of monocytes or lymphocytes but do not appear to be chemoattractants for neutrophils. Chemokines, such as RANTES and MIP-1α, have been implicated in a wide range of human acute and chronic inflammatory diseases including respiratory diseases, such as asthma and allergic disorders.

The chemokine receptors are members of a superfamily of G protein-coupled receptors (GPCR) which share structural features that reflect a common mechanism of action of signal transduction (Gerard, C. and Gerard, N. P., *Annu Rev. Immunol.*, 12:775–808 (1994); Gerard, C. and Gerard, N. P., *Curr. Opin. Immunol.*, 6:140–145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse. The first receptor for the C-C chemokines that was cloned and expressed binds the chemokines MIP-1α and RANTES. Accordingly, this MIP-1α/RANTES receptor was designated C-C chemokine receptor 1 (also referred to as CCR-1; Neote, K., et al., *Cell*, 72:415–425 (1993); Horuk, R. et al., WO 94/11504, May 26, 1994; Gao, J.-I. et al., *J. Exp. Med.*, 177:1421–1427 (1993)). Three receptors have been characterized which bind and/or signal in response to RANTES: CCR3 mediates binding and signaling of chemokines including eotaxin, RANTES, and MCP-3 (Ponath et al., *J. Exp. Med.*, 183:2437 (1996)), CCR4 binds chemokines including RANTES, MIP-1α, and MCP-1 (Power, et al., *J. Biol. Chem.*, 270:19495 (1995)), and CCR5 binds chemokines including MIP-1α, RANTES, and MIP-1β (Samson, et al., *Biochem.* 35: 3362–3367 (1996)). RANTES is a chemotactic chemokine for a variety of cell types, including monocytes, eosinophils, and a subset of T-cells. The responses of these different cells may not all be mediated by the same receptor, and it is possible that the receptors CCR1, CCR4 and CCR5 will show some selectivity in receptor distribution and function between leukocyte types, as has already been shown for CCR3 (Ponath et al.). In particular, the ability of RANTES to induce the directed migration of monocytes and a memory population of circulating T-cells (Schall, T. et al., *Nature*, 347:669–71 (1990)) suggests this chemokine and its receptor(s) may play a critical role in chronic inflammatory diseases, since these diseases are characterized by destructive infiltrates of T cells and monocytes.

Many existing drugs have been developed as antagonists of the receptors for biogenic amines, for example, as antagonists of the dopamine and histamine receptors. No successful antagonists have yet been developed to the receptors for the larger proteins such as chemokines and C5a. Small molecule antagonists of the interaction between C-C chemokine receptors and their ligands, including RANTES and MIP-1α, would provide compounds useful for inhibiting harmful inflammatory processes "triggered" by receptor ligand interaction, as well as valuable tools for the investigation of receptor-ligand interactions.

SUMMARY OF THE INVENTION

It has now been found that a class of small organic molecules are antagonists of chemokine receptor function and can inhibit leukocyte activation and/or recruitment. An antagonist of chemokine receptor function is a molecule which can inhibit the binding and/or activation of one or more chemokines, including C-C chemokines such as RANTES, MIP-1α, MCP-2, MCP-3 and MCP-4 to one or more chemokine receptors on leukocytes and/or other cell types. As a consequence, processes and cellular responses mediated by chemokine receptors can be inhibited with these small organic molecules. Based on this discovery, a method of treating a disease associated with aberrant leukocyte recruitment and/or activation is disclosed as well as a method of treating a disease mediated by chemokine receptor function. The method comprises administering to a subject in need an effective amount of a compound or small organic molecule which is an antagonist of chemokine receptor function. Compounds or small organic molecules which have been identified as antagonists of chemokine receptor function are discussed in detail herein below, and can be used for the manufacture of a medicament for treating or for preventing a disease associated with aberrant leukocyte recruitment and/or activation. The invention also relates to the disclosed compounds and small organic molecules for use in treating or preventing a disease associated with aberrant leukocyte recruitment and/or activation. The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with aberrant leukocyte recruitment and/or activation and methods for their preparation.

DETAILED DESCRIPTION OF THE INVENTION

Figure 1:
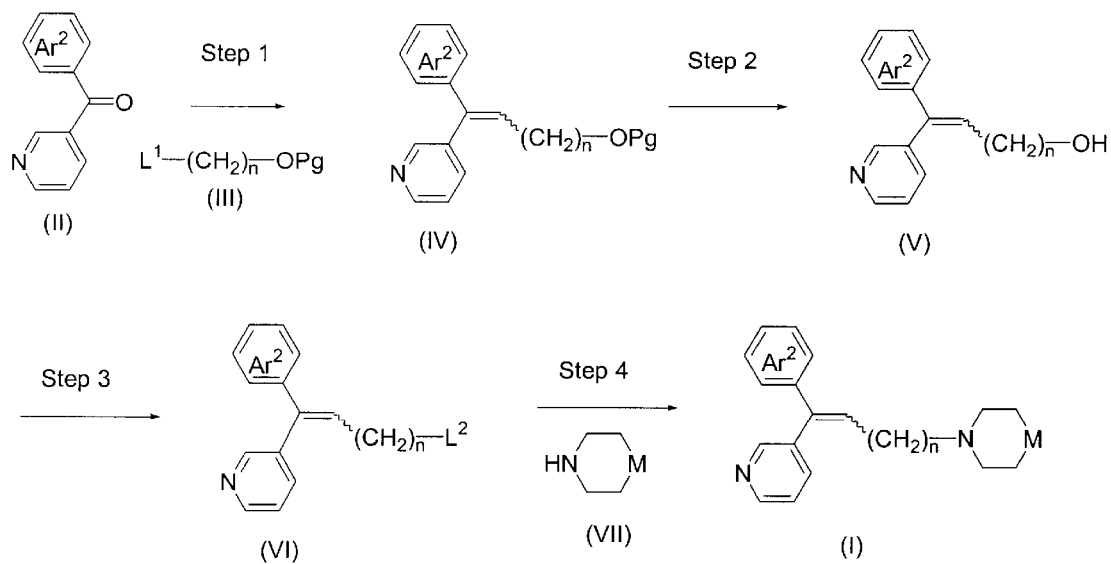
FIG. 1 is a schematic showing the preparation of the compounds represented by Structural Formula (I).

The present invention relates to small molecule compounds which are modulators of chemokine receptor function. In a preferred embodiment, the small molecule compounds are antagonists of chemokine receptor function. Accordingly, processes or cellular responses mediated by the binding of a chemokine to a receptor can be inhibited (reduced or prevented, in whole or in part), including leukocyte migration, integrin activation, transient increases in the concentration of intracellular free calcium $[Ca^{++}]_i$, and/or granule release of proinflammatory mediators.

The invention further relates to a method of treatment, including prophylactic and therapeutic treatments, of a disease associated with aberrant leukocyte recruitment and/or activation or mediated by chemokines or chemokine receptor function, including chronic inflammatory disorders characterized by the presence of RANTES, MIP-1α, MCP-2, MCP-3 and/or MCP-4 responsive T cells, monocytes and/or eosinophils, including but not limited to diseases such as arthritis, psoriasis, multiple sclerosis, inflammatory bowel diseases such as ulcerative colitis and Crohn's disease, rejection of transplanted organs and tissues (i.e., allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with Human Immunodeficiency Virus (HIV) infection, e.g., AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to the subject in need of treatment an effective amount of a compound (i.e., one or more compounds) which inhibits chemokine receptor function, inhibits the binding of a chemokine to leukocytes and/or other cell types, and/or which inhibits leukocyte migration to, and/or activation at, sites of inflammation.

The invention further relates to methods of antagonizing a chemokine receptor, such as CCR1, in a mammal comprising administering to the mammal a compound as described herein.

According to the method, chemokine-mediated chemotaxis and/or activation of pro-inflammatory cells bearing receptors for chemokines can be inhibited. As used herein, "pro-inflammatory cells" includes but is not limited to leukocytes, since chemokine receptors can be expressed on other cell types, such as neurons and epithelial cells.

While not wishing to be bound by any particular theory or mechanism, it is believed that compounds of the invention are antagonists of the chemokine receptor CCR1, and that therapeutic benefits derived from the method of the invention are the result of antagonism of CCR1 function. Thus, the method and compounds of the invention can be used to treat a medical condition involving cells which express CCR1 on their surface and which respond to signals transduced through CCR1, as well as the specific conditions recited above.

The antagonist of chemokine receptor function is represented by Structural Formula (I):

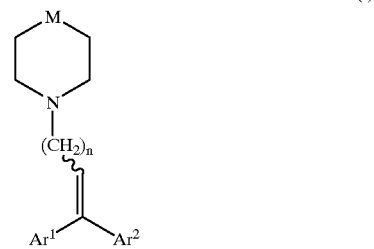

(I)

and physiologically acceptable salts thereof.

$Ar^1$ is a heteroaryl group, and $Ar^2$ is a carbocyclic aromatic or heteroaryl group.

n is an integer, such as an integer from one to about four. Preferably, n is one, two or three. More preferably n is two. In alternative embodiments, other aliphatic or aromatic spacer groups (L) can be employed for $(CH_2)_n$.

M is $>NR^2$ or $>CR^1R^2$. M is preferably $>C(OH)R^2$.

$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group) or —O—C(O)-(substituted aliphatic group), —COOH, —CN, —CO—$NR^3R^4$ or —$NR^3R^4$. $R^1$ is preferably —H or —OH.

$R^2$ is —H, —OH, an acyl group, a substituted acyl group, —$NR^5R^6$, an aliphatic group, a substituted aliphatic group, an aromatic group, a substituted aromatic group, a benzyl group, a substituted benzyl group, a non-aromatic heterocyclic group or a substituted non-aromatic heterocyclic group. $R^2$ is preferably an aromatic group or a substituted aromatic group.

$R^3$, $R^4$, $R^5$ and $R^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

$R^1$ and $R^2$, $R^3$ and $R^4$, or $R^5$ and $R^6$ taken together with the atom to which they are bonded, can alternatively form a substituted or unsubstituted non-aromatic carbocyclic or heterocyclic ring.

$Ar^1$ and $Ar^2$ in Structural Formula (I) can be independently substituted or unsubstituted. Suitable substituents are as described herein below. In one example, $Ar^1$ and/or $Ar^2$ is substituted with $-(O)_u-(CH_2)_t-COOR^{20}$, $-(O)_u-(CH_2)_t-C(O)-NR^{21}R^{22}$ or $-(O)_u-(CH_2)_t-NHC(O)-O-R^{20}$.

u is zero or one.

t is an integer, such as an integer from zero to about three. The methylene group, $-(CH_2)_t-$, can be substituted or unsubstituted.

$R^{20}$, $R^{21}$ or $R^{22}$ are independently —H, an aliphatic group, a substituted aliphatic group, an aromatic group, a substituted aromatic group or a non-aromatic heterocyclic group. Alternatively, $R^{21}$ and $R^{22}$, taken together with the nitrogen atom to which they are bonded, form a non-aromatic heterocyclic ring.

In one embodiment, $Ar^1$ is a 3-pyridyl group, $Ar^2$ is a carbocyclic aromatic or heteroaromatic group and $Ar^1$ and $Ar^2$ are independently substituted or unsubstituted.

In a preferred embodiment the antagonist of chemokine receptor function is represented by Structural Formula (II), wherein Ar¹ is a 3-pyridyl group, Ar² is a phenyl group and Ar¹ and Ar² are independently substituted or unsubstituted.

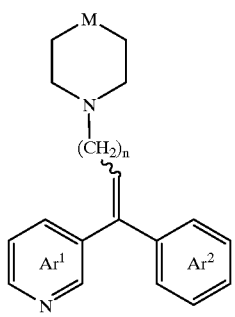

(II)

Preferably Ar² in Structural Formula (II) bears a meta substituent, R⁴⁰, and the antagonist of chemokine receptor function is represented by Structural Formula (III):

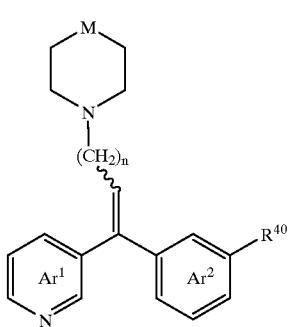

(III)

wherein R⁴⁰ can be —OH, halogen, substituted or unsubstituted aliphatic group, substituted or unsubstituted aromatic group, —O-(aliphatic group), —O-(substituted aliphatic group), —O-(aromatic group), —O-(substituted aromatic group, electron withdrawing group, —(O)$_u$—(CH$_2$)$_t$—COOR²⁰, —(O)$_u$—(CH$_2$)$_t$—C(O)—NR²¹R²² or —(O)$_u$, —(CH$_2$)$_t$—NHC(O)—O—R²⁰.

u can be zero or one.

t is an integer, such as an integer from zero to about three.

R²⁰, R²¹ or R²² can independently be —H, an aliphatic group, a substituted aliphatic group, an aromatic group, a substituted aromatic group or a non-aromatic heterocyclic group. Alternatively, R²¹ and R²², taken together with the nitrogen atom to which they are bonded, form a non-aromatic heterocyclic ring.

Preferably R⁴⁰ is an aliphatic group, —O-(aliphatic group) or —O-(substituted aliphatic group). More preferably, R⁴⁰ is —O-alkyl, such as —O—CH₃, —O—C₂H₅, —O—C₃H₇ or —O—C₄H₉.

Another embodiment provides novel compounds employed in these methods.

The double bond-containing compounds disclosed herein can be obtained as E- and Z-configurational isomers. It is expressly pointed out that the invention includes compounds of the E-configuration and the Z-configuration around the double bond, and a method of treating a subject with compounds of the E-configuration, the Z-configuration, and mixtures thereof. Accordingly, in the structural formulas presented herein, the symbol:

is used to represent both E-configuration and the Z-configuration. Preferably Ar¹ and the (CH₂)$_n$ moiety are in the cis configuration. For example, the compounds can have the configuration of:

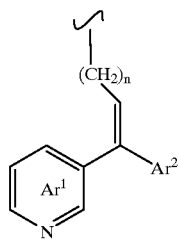

It is understood that one configuration can have greater activity than another. The desired configuration can be determined by screening for activity, employing the methods described herein.

Additionally, certain compounds of the invention may be obtained as different sterioisomers (e.g., diastereomers and enantiomers). It is pointed out that the invention includes all isomeric forms and racemic mixtures of the disclosed compounds and a method of treating a subject with both pure isomers and mixtures thereof, including racemic mixtures. Again, it is understood that one sterioisomer may be more active than another. The desired isomer can be determined by screening.

Also included in the present invention are physiologically acceptable salts of the compounds represented by Structural Formulas (I) through (III). Salts of compounds containing an amine or other basic group can be obtained, for example, by reacting with a suitable organic or inorganic acid, such as hydrogen chloride, hydrogen bromide, acetic acid, citric acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium, ammonium, calcium and the like.

As used herein, aliphatic groups include straight chained, branched or cyclic C₁–C₂₀ hydrocarbons which are completely saturated or which contain one or more units of unsaturation. For example, suitable aliphatic groups include substituted or unsubstituted linear, branched or cyclic C₁–C₂₀ alkyl, alkenyl or alkynyl groups.

Aromatic groups include carbocyclic aromatic groups such as phenyl, 1-naphthyl, 2-naphthyl, 1-anthracyl and 2-anthracyl, and heterocyclic aromatic or heteroaryl groups such as N-imidazolyl, 2-imidazolyl, 4-imidazolyl, 5-imidazolyl, 2-thienyl, 3-thienyl, 2-furanyl, 3-furanyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 4-pyridazinyl, 3-pyrazolyl, 4-pyrazolyl, 5-pyrazolyl, 2-pyrazinyl, 2-thiazolyl, 4-thiazolyl, 5-thiazolyl, 5-tetrazolyl, 2-oxazolyl, 4-oxazolyl and 5-oxazolyl. Where these rings are fused, for example, to a non-aromatic or aromatic ring, the stated point of attachment can be either of the two fused bonds.

Aromatic groups also include fused polycyclic aromatic ring systems in which a carbocyclic aromatic ring or heteroaryl ring is fused to one or more other rings. Examples include tetrahydronaphthyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 2-quinolinyl, 3-quinolinyl, 1-isoquinolinyl, 3-quinolinyl, 1-isoindolyl, 3-isoindolyl, and acridinyl. Also included within the scope of the term "aromatic group", as it is used herein, is a group in which one or more carbocyclic aromatic rings and/or heteroaryl rings are fused to a cycloalkyl or non-aromatic heterocyclic ring.

The term "non-aromatic ring" includes non-aromatic carbocyclic rings and non-aromatic heterocyclic rings. Non-aromatic heterocyclic rings are non-aromatic carbocyclic rings which include one or more heteroatoms such as nitrogen, oxygen or sulfur in the ring. The ring can be five, six, seven or eight-membered and/or fused to another ring, such as a cycloalkyl on aromatic ring. Examples of non-aromatic rings include, for example, 3-1H-benzimidazol-2-one, 3-1-alkyl-benzimidazol-2-one, 3-1-methyl-benzimidazol-2-one, 2-tetrahydrofuranyl, 3-tetrahydrofuranyl, 2-tetrahyrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidyl, 1-3-alkyl-phthalimidyl, tetrahydronapthyl, benzocyclopentane, benzocyclohexane, benzoxane, benzopyrolidine, benzopiperidine, benzoxolane, benzothiolane, benzothiane,

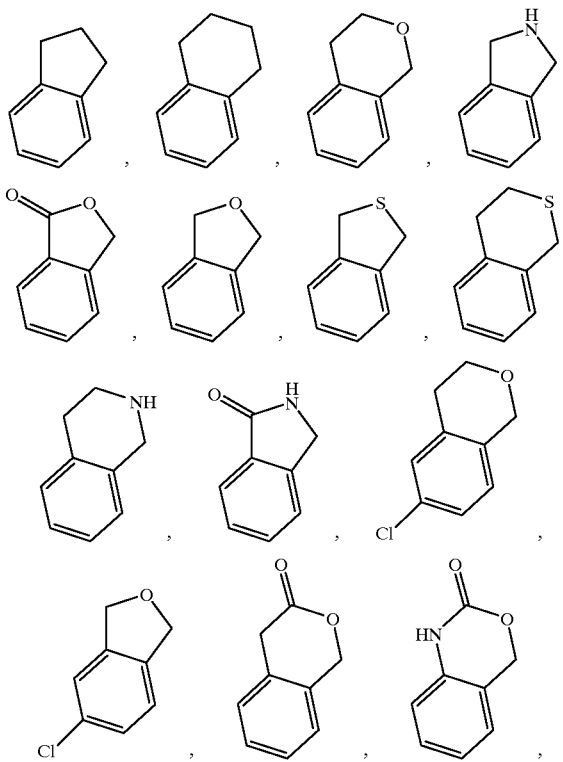

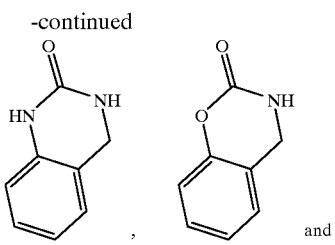

-continued

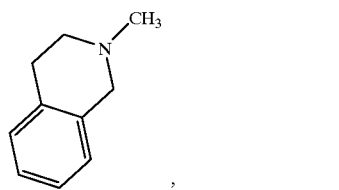

and

Suitable substituents on an aliphatic group, aromatic group (carbocyclic and heteroaryl), non-aromatic heterocyclic ring or benzyl group include, for example, an electron withdrawing group, a halogen, —CN, —COOH, —OH, —CONR$^{24}$R$^{25}$, —NR$^{24}$R$^{25}$, —OS(O)$_2$NR$^{24}$R$^{25}$, —S(O)$_2$NR$^{24}$R$^{25}$, —SO$_3$H, —S(O)$_2$NH$_2$, guanidino, —(CH$_2$)$_t$—COOH, —(CH$_2$)$_t$—COOR$^{20}$, —(CH$_2$)$_t$—C(O)—NR$^{21}$R$^{22}$, —Q—H, —Q-(aliphatic group), —Q-(substituted aliphatic group), —Q-(aryl), —Q—(CH$_2$)$_p$-(substituted or unsubstituted aromatic group) (p is an integer from 1–5), —Q-(non-aromatic heterocyclic group) or —Q—(CH$_2$)$_p$-(non-aromatic heterocyclic group).

R$^{20}$, R$^{21}$ or R$^{22}$ are independently —H, an aliphatic group, a substituted aliphatic group, an aromatic group, a substituted aromatic group, —NHC(O)—O-(aliphatic group), —NHC(O)—O-(aromatic group) or —NHC(O)—O-(non-aromatic heterocyclic group) and wherein R$^{21}$ and R$^{22}$, taken together with the nitrogen atom to which they are bonded, can form a non-aromatic heterocyclic ring.

t is an integer from zero to about three.

Q is —O—, —S—, —S(O)—, —S(O)$_2$ —, —OS(O)$_2$, —C (O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$^{23}$)—, —C(NR$^{23}$)NHNH— or —NHNHC(NR$^{23}$)—.

R$^{23}$ is —H, an aliphatic group, a benzyl group, an aryl group or non-aromatic heterocyclic group.

R$^{24}$ and R$^{25}$ are independently —H, an aliphatic group, a benzyl group, an aryl group or non-aromatic heterocyclic group.

A substituted non-aromatic heterocyclic ring, benzyl group or aromatic group can also have an aliphatic or substituted aliphatic group as a substituent. A substituted aliphatic group can also have an oxo group, epoxy group, non-aromatic heterocyclic ring, benzyl group, substituted benzyl group, aromatic group or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

Acyl groups include substituted and unsubstituted aliphatic carbonyl, aromatic carbonyl, aliphatic sulfonyl and aromatic sulfonyl.

Suitable electron withdrawing groups include, for example, alkylimines, alkylsulfonyl, carboxamido, carboxylic alkyl esters, —CH=NH, —CN, —NO$_2$ and halogens.

A "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of a compound is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium $[Ca^{2+}]_i$ and granule release of proinflammatory mediators. Alternatively, an "effective amount" of a compound is a quantity sufficient to achieve a desired therapeutic and/or prophylactic effect, such as an amount which results in the prevention of or a decrease in the symptoms associated with a disease associated with aberrant leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchodilators, corticosteroids, antihistamines, antiallergic agents and the like.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), transdermally, topically, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical carrier as part of a pharmaceutical composition for treatment of HIV infection, inflammatory disease, or the other diseases discussed above. Formulation of a compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The activity of compounds of the present invention can be assessed using suitable assays, such as receptor binding assays and chemotaxis assays. For example, as described in the Exemplification Section, small molecule antagonists of RANTES and MIP-1α binding have been identified utilizing THP-1 cells which bind RANTES and chemotax in response to RANTES and MIP-1α as a model for leukocyte chemotaxis. Specifically, a high through-put receptor binding assay, which monitors $^{125}$I-RANTES and $^{125}$I-MIP-1α binding to THP-1 cell membranes, was used to identify small molecule antagonists which block binding of RANTES and MIP-1α. Compounds of the present invention can also be identified by virtue of their ability to inhibit the activation steps triggered by binding of a chemokine to its receptor, such as chemotaxis, integrin activation and granule mediator release. They can also be identified by virtue of their ability to block RANTES and MIP-1α mediated HL-60, T-cell, peripheral blood mononuclear cell, and eosinophil chemotactic response.

The compounds disclosed herein can be prepared accordingly to the schemes shown in FIGS. 1–5. The schemes are described in greater detail below.

FIG. 1 shows the preparation of compounds represented by Structural Formula (I). $L^1$ is $PPh_3Cl$, $PPh_3Br$, $PPh_3I$ or $(EtO)_2P(O)$, $L^2$ is a suitable leaving group such as halogen, p-toluene sulfonate, mesylate, alkoxy, and phenoxy; Pg is a suitable protecting group such as tetrahydropyranyl; and the other symbols are as defined above.

In Step 1 of FIG. 1, a Wittig reaction is carried out in a solvent such as ether, or tetrahydrofuran (THF) in the presence of a base such as sodium hydride, n-butyl lithium or lithium diisopropylamide (LDA) at 0° C. up to the reflux temperature for the solvent used for 5 minutes to 72 h. Compounds represented by Formula II in FIG. 1 can be prepared by methods disclosed in J. Med. Chem., 1992 (35) 2074–2084, the entire teachings of which are incorporated herein by reference.

In Step 2 of FIG. 1, deprotection is carried out with an acid in a solvent such as methanol at room temperature up to the reflux temperature for the solvent used for 5 minutes to 72 h. Alternatively, a compound of represented by Formula V in FIG. 1 can be prepared directly from step 1 without isolating an intermediate. The reaction mixture obtained after the work up of the reaction described in step 1 can be dissolved in the solvent and reacted with the acid.

In Step 3 of FIG. 1, the hydroxy group can be converted to a leaving group by known methods. Compounds represented by Formula VI in FIG. 1 can be prepared by methods disclosed in J. Med. Chem., 1992 (35) 2074–2084 and J. Org. Chem., 1977 (42) 353.

In Step 4 of FIG. 1, an alkylation reaction is carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 2:
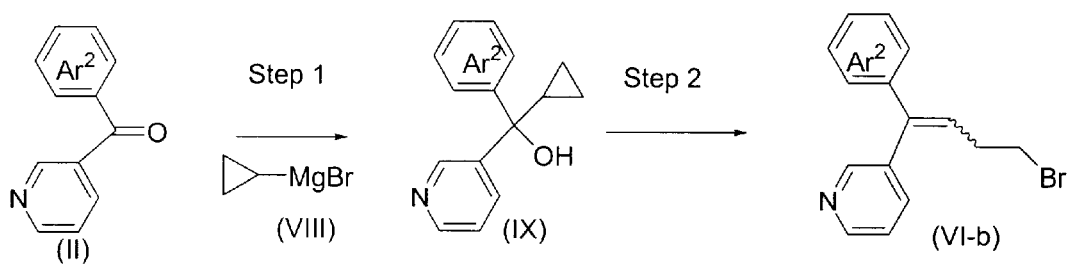
FIG. 2 is a schematic showing the preparation of the compounds represented by Compound (VI-b).

FIG. 2 shows the preparation of compounds represented by Compound (VI-b). In Step 1 of FIG. 2, a Grignard reaction may be carried out in a solvent such as ether, or tetrahydrofuran (THF) at 0° C. up to the reflux temperature for the solvent used for 5 minuets to 72 h. Compound VII is available commercially.

In Step 2 of FIG. 2, bromination may be carried out with brominate agents such as hydrobromic acid, bromotrimethylsilane or boron tribromide-methyl sulfide complex in a solvent such as acetic acid, dichloromethane or dichloroethane at room temperature up to the reflux temperature for the solvent used for 5 minutes to 72 h.

Figure 3:
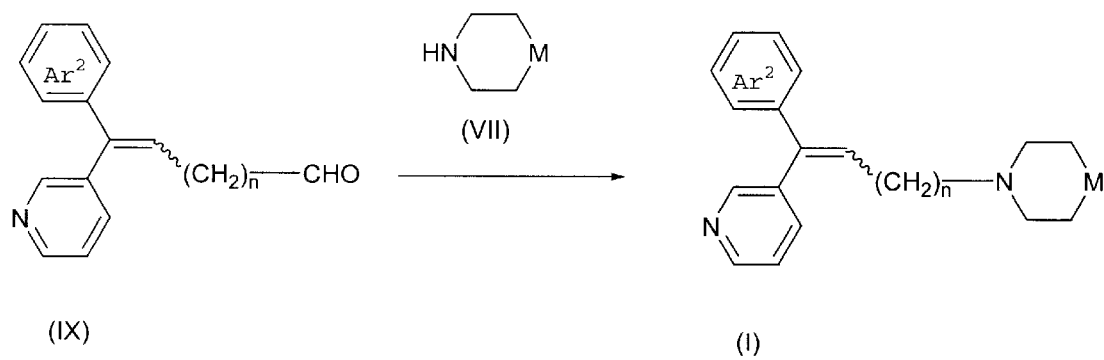
FIG. 3 is a schematic showing the preparation of the compounds represented by Structural Formula (I)

FIG. 3 shows the preparation of compounds represented by Structural Formula (I). In FIG. 3, a reductive amination may be carried out with reducing regents such as sodium cyanoborohydride, sodium acetoxyborohydride or sodium borohydride in a solvent such as methanol, ethanol, tetrahydrofuran (THF), dichloromethane or dichloroethane at room temperature up to the reflux temperature for the solvent used for 5 minutes to 72 h.

Figure 4:
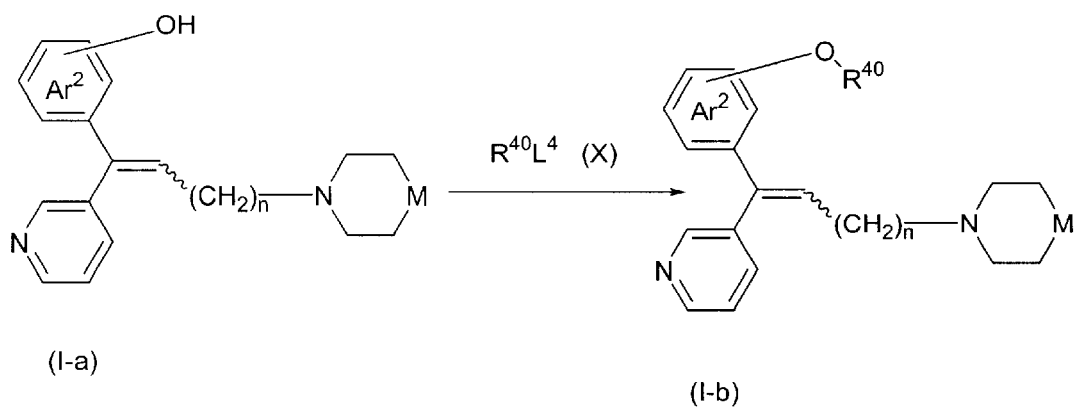
FIG. 4 is a schematic showing the preparation of representative compounds of Structural Formula (I), wherein $Ar^1$ and/or $Ar^2$ can be substituted with $R^{40}$.

FIG. 4 shows the preparation of representative compounds represented of Structural Formula (I), wherein $Ar^1$ and/or $Ar^2$ can be substituted with $R^{40}$. In FIG. 4, an alkylation reaction may be carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 5:
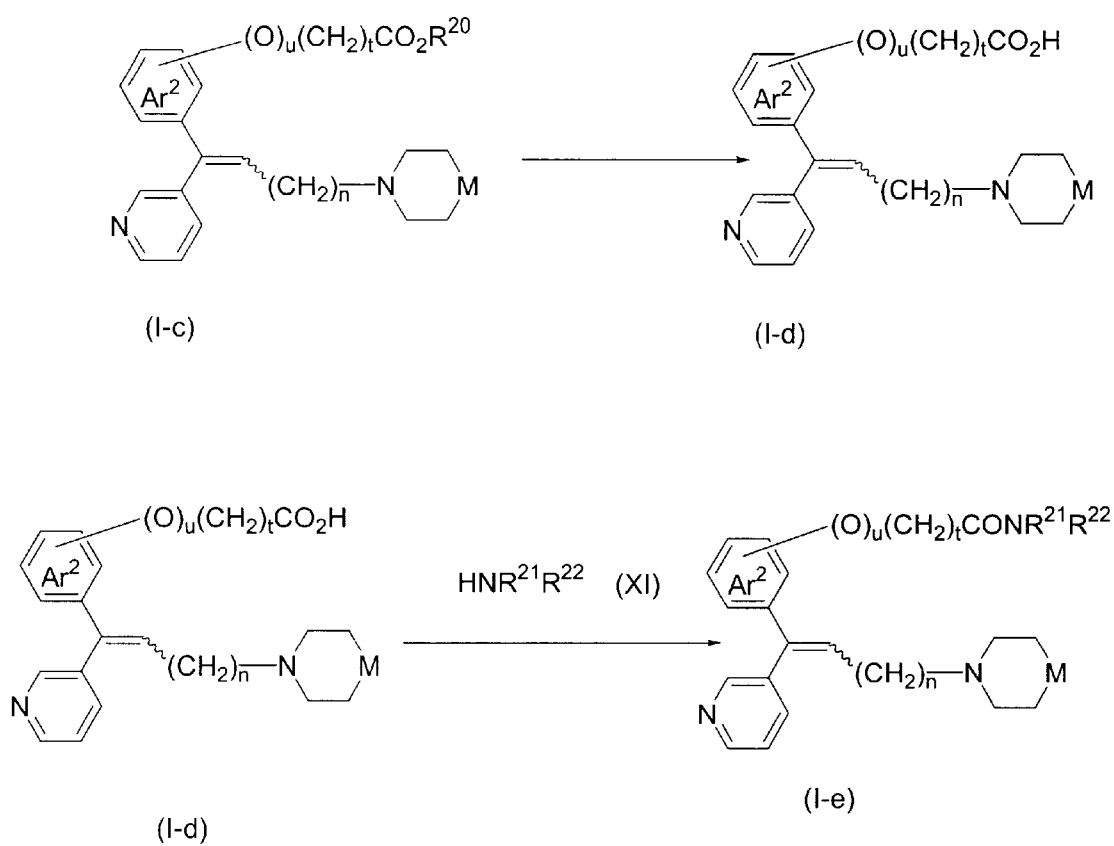
FIG. 5 is a schematic showing the preparation of representative compounds of Structural Formula (I), wherein $Ar^1$ and/or $Ar^2$ can be substituted with $-(O)_u-(CH_2)_t-COOR^{20}$, $-(O)_u-(CH_2)_t-C(O)-NR^{21}R^{22}$ or $-(O)_u-(CH_2)_t-NHC(O)O-R^{20}$.
Figure 6A:
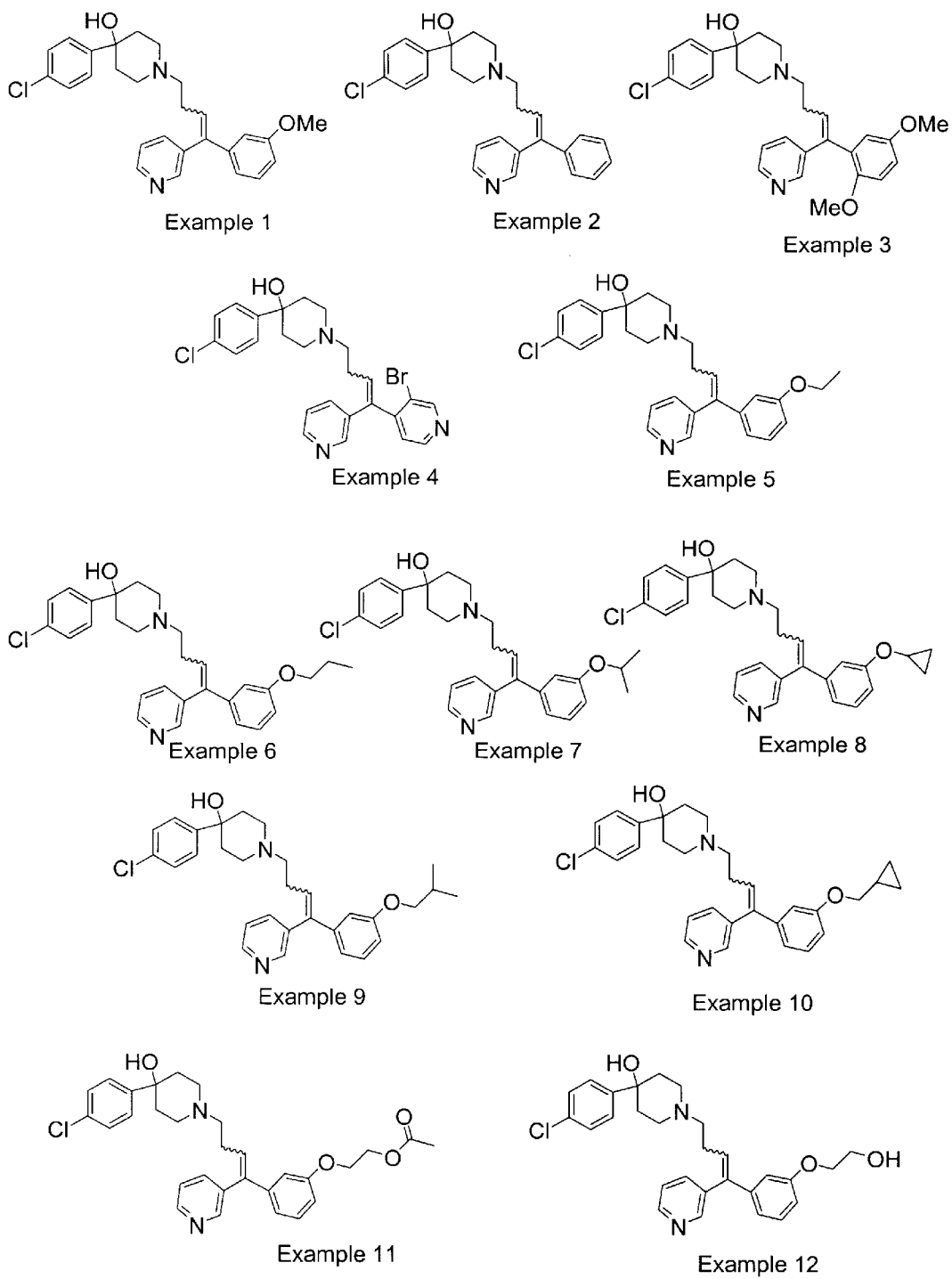
FIGS. 6A–6G show the structures of exemplary compounds of the present invention.
Figure 6B:
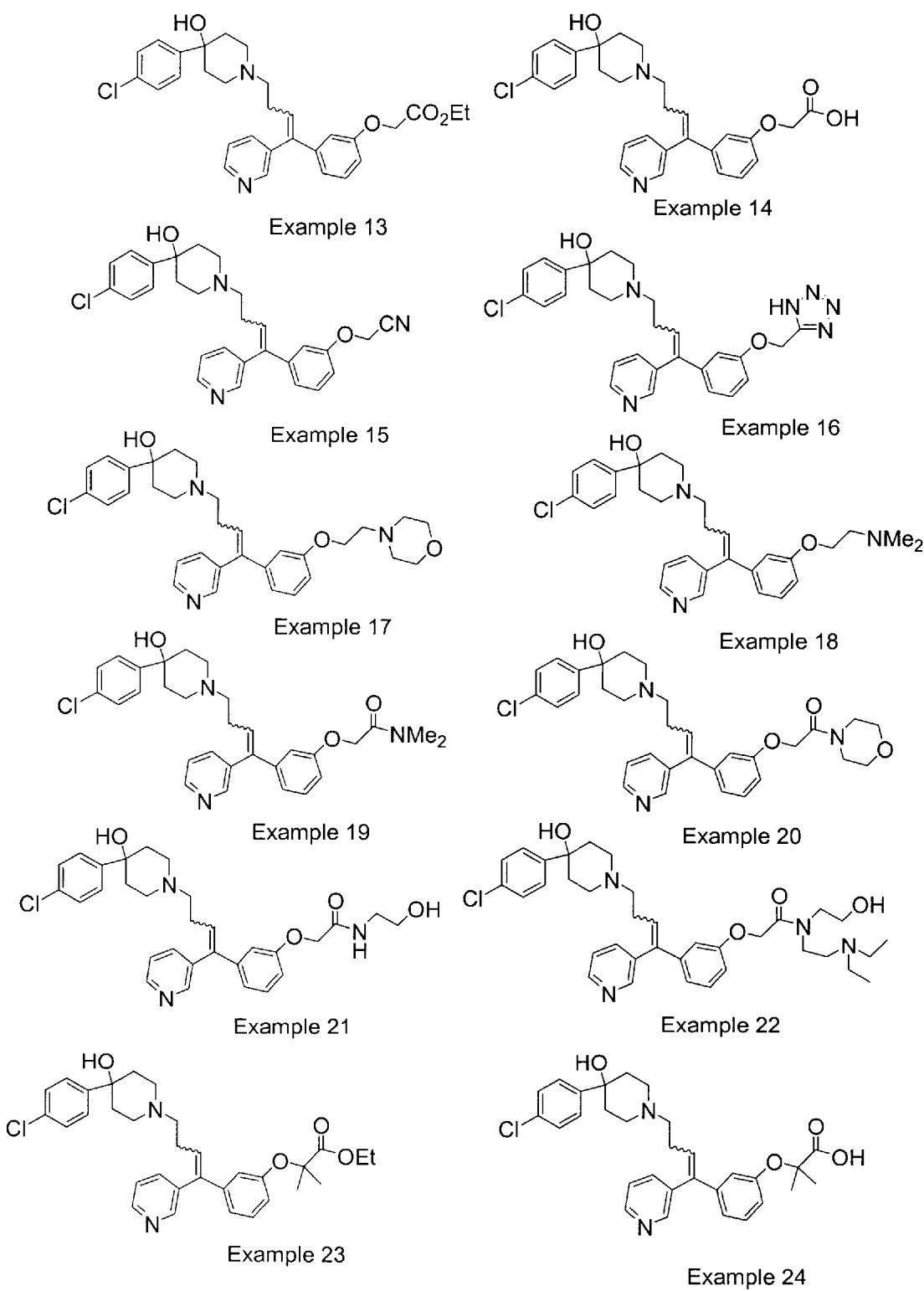
Figure 6C:
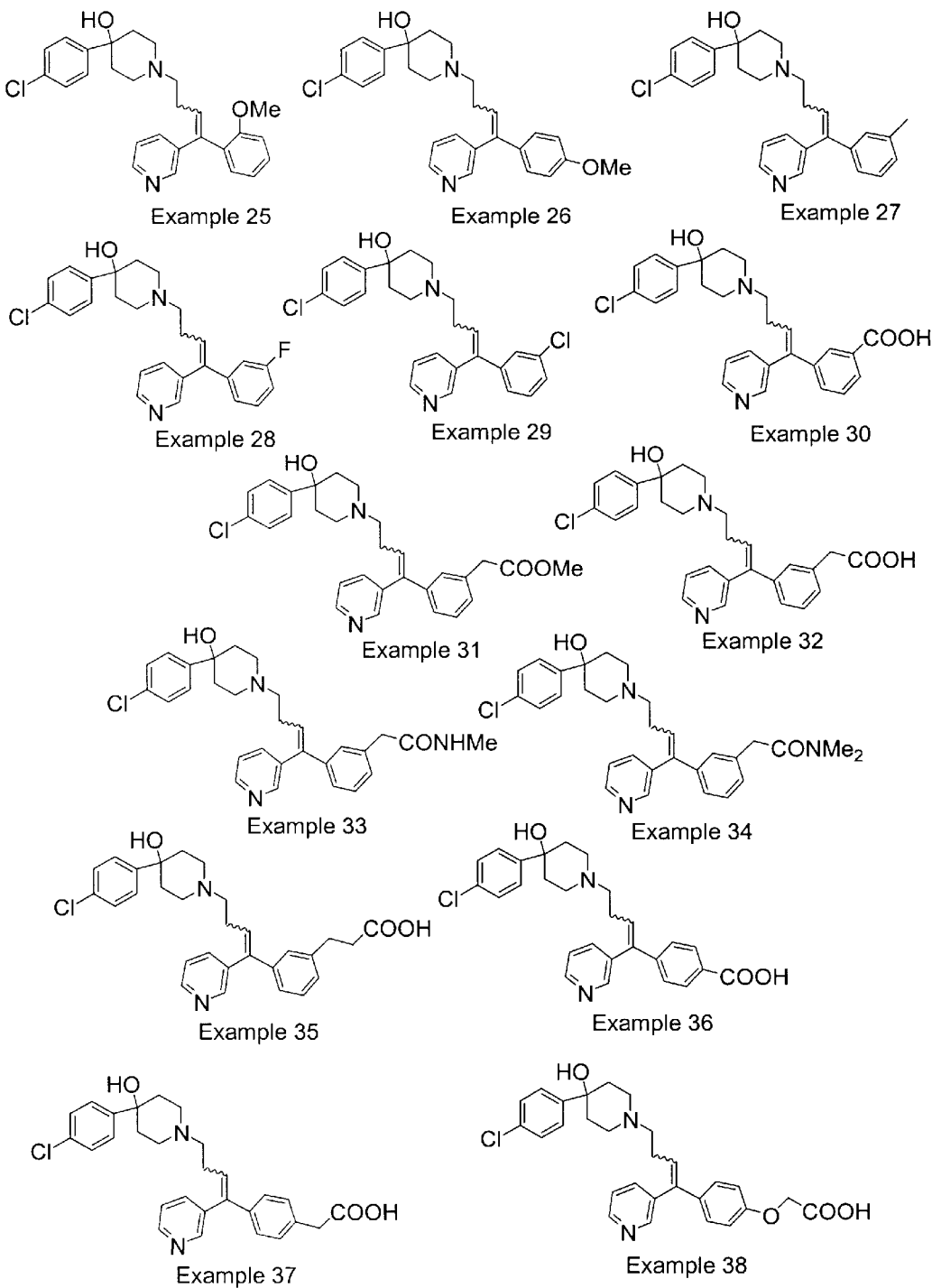
Figure 6D:
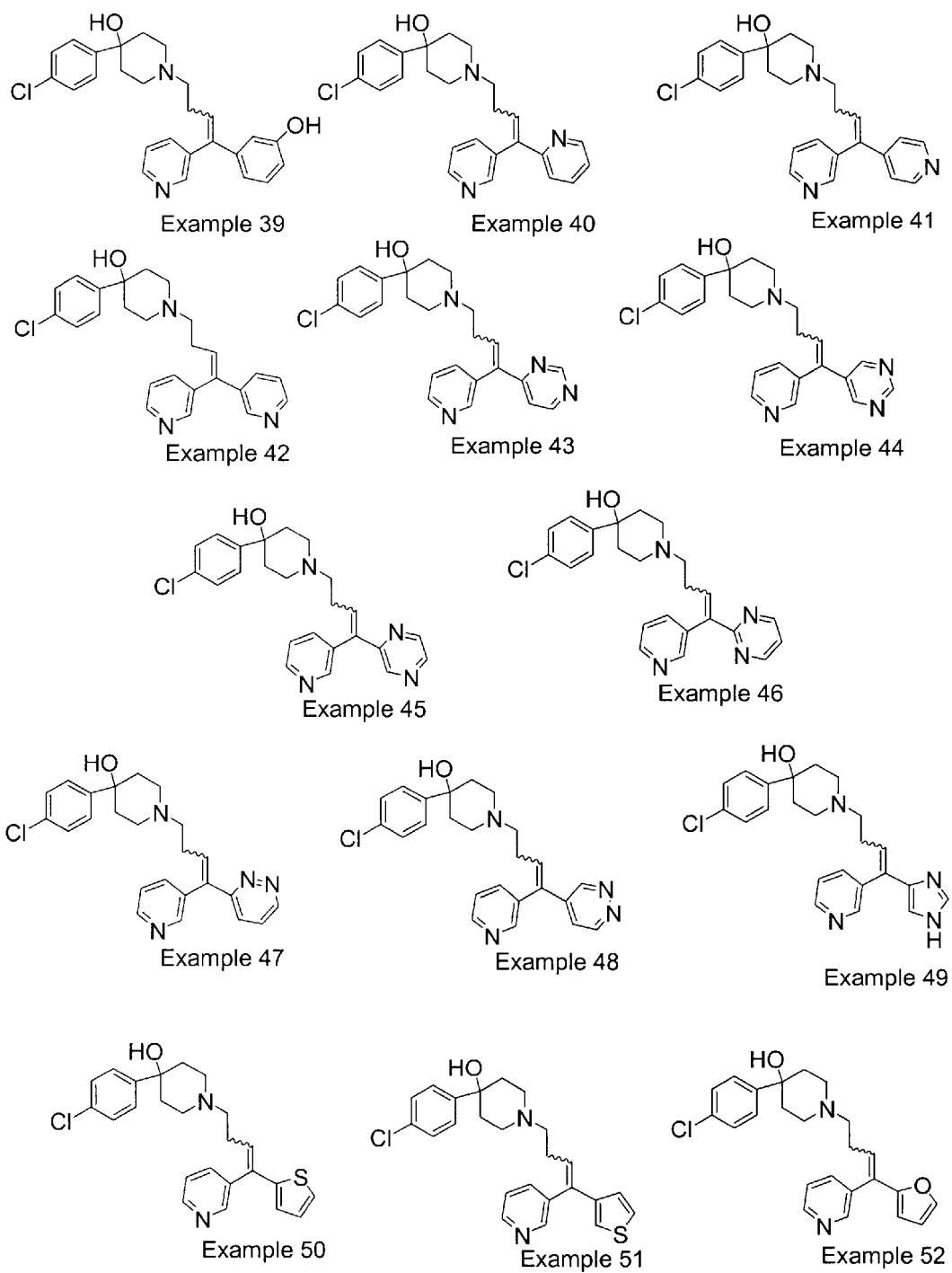
Figure 6E:
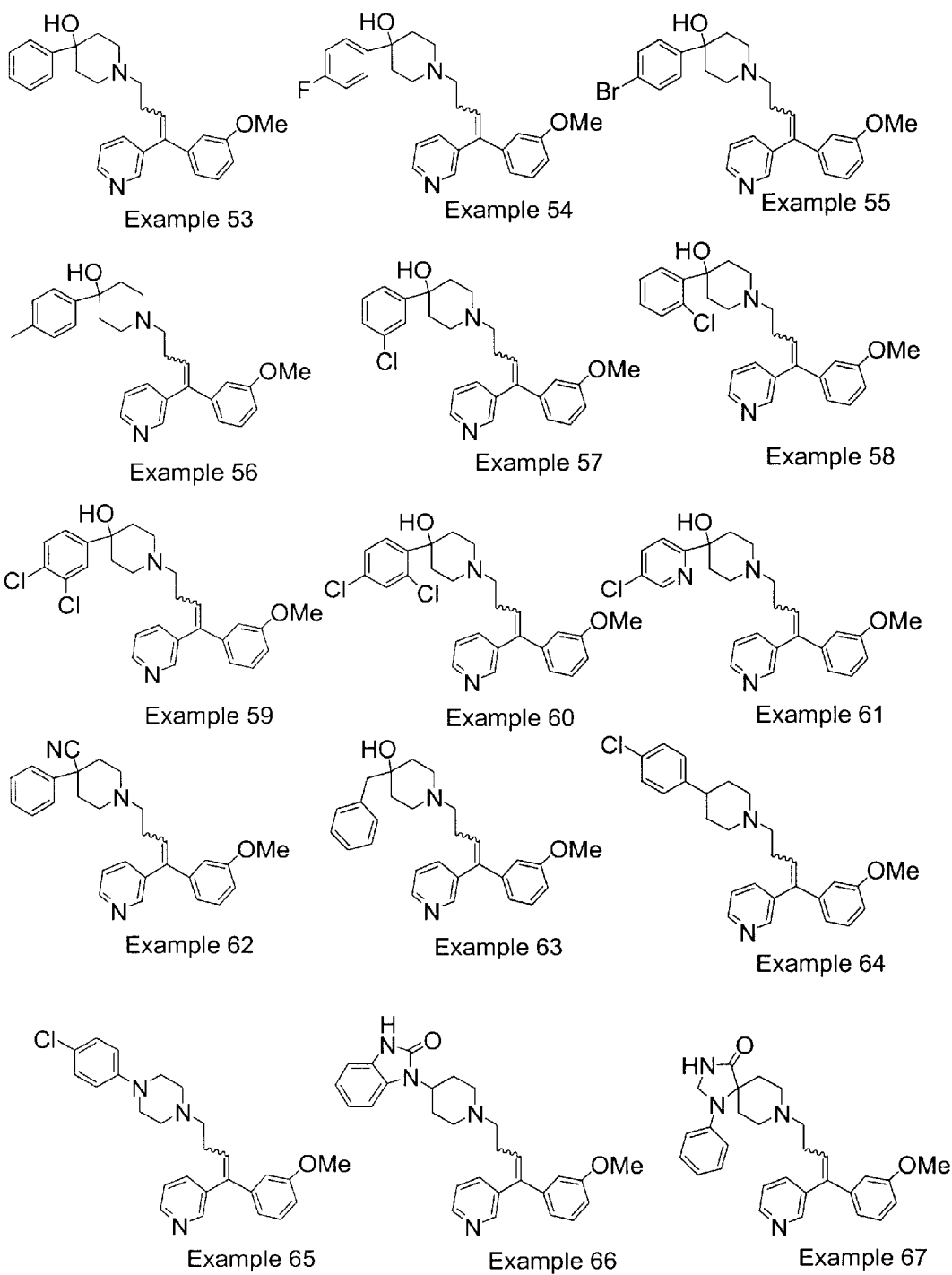
Figure 6F:
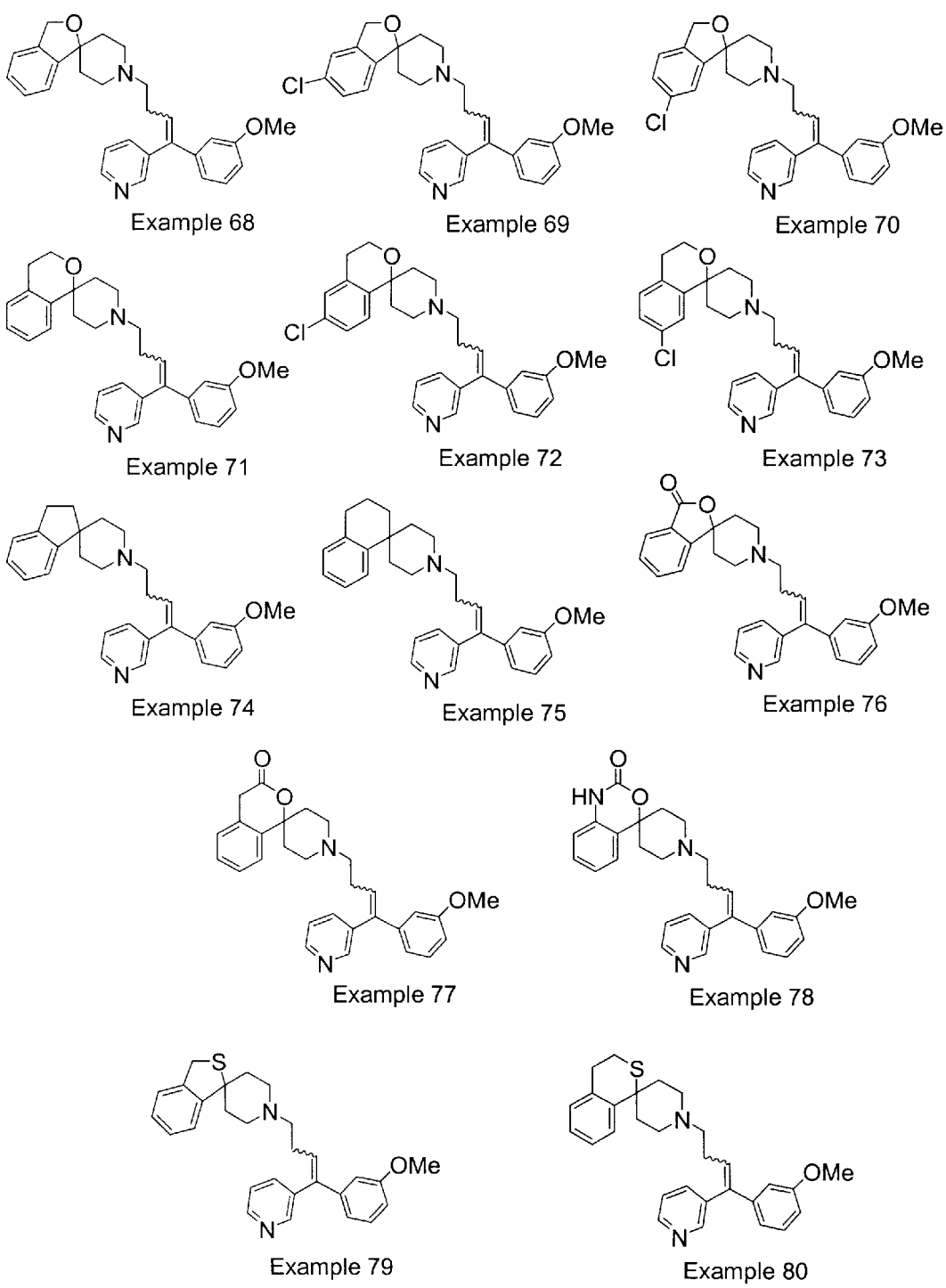
Figure 6G:
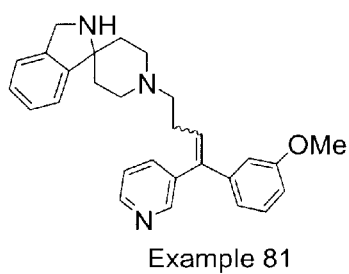
Figure 6G:
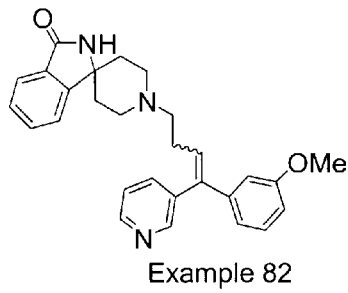
Figure 6G:
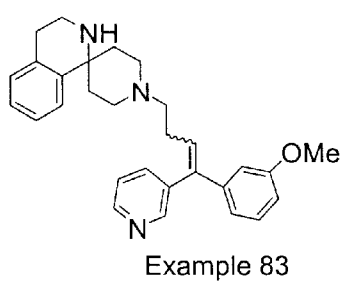
Figure 6G:
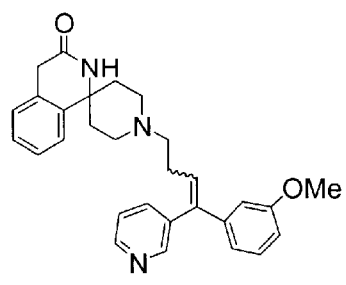
Figure 6G:
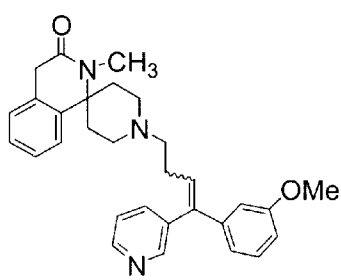
Figure 6G:
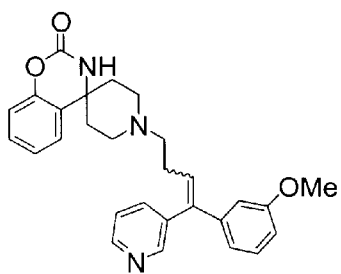
Figure 6G:
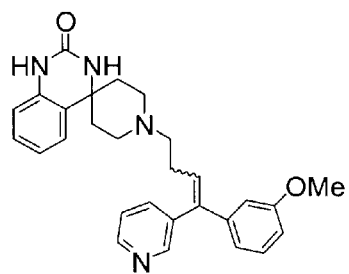
Figure 6G:
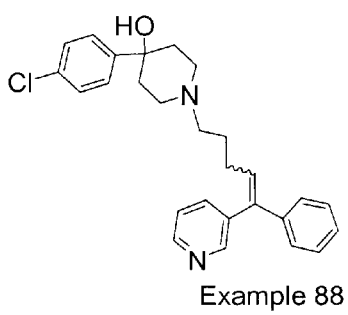
Figure 6G:
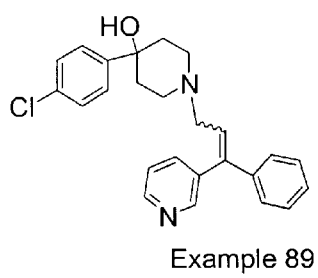
Figure 6G:
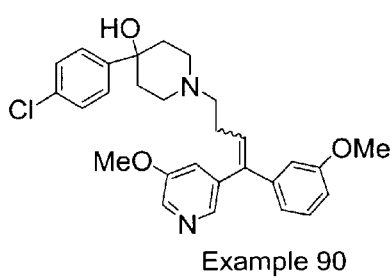

FIG. 5 is a schematic showing the preparation of representative compounds of Structural Formula (I), wherein $Ar^1$ and/or $Ar^2$ can be substituted with —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)O—R$^{20}$. In FIG. 5, the hydrolysis reaction may be carried out in a mixture of aqueous alkali metal hydroxide solution and a solvent such as methanol, ethanol, tetrahydrofuran (THF) or dioxane at room temperature up to the reflux temperature for the solvent used for 5 minutes to 72 h. The acylation reaction can be carried out using dicyclohexylcarbodiimide (DCC) or (1-ethyl-3-(3-dimethylaminopropyl)carbodiimide (DEC) in a solvent such as tetrahydrofuran (THF), dimethylformamide (DMF) or methylene chloride in the presence of a base such as pyridine or triethylamine (when necessary) at temperatures of 0 to 100° C. for 5 minutes to 72 h.

Although FIGS. 1–5 show the preparation of compounds in which $Ar^1$ is 3-pyridyl and $Ar^2$ is phenyl, analogous compounds with other heteroaryl groups for $Ar^1$ and/or $Ar^2$ can be prepared by using starting materials with heteroaryl groups in the corresponding positions. These starting materials can be prepared according to methods which are known to those of skill in the art.

The invention is illustrated by the following examples which are not intended to be limiting in any way.

EXEMPLIFICATION

Example 1

4-(4-Chlorophenyl)-1-[4-(3-methoxyphenyl)-4-(3-pyridinyl)-3-butenyl]piperidin-4-ol Step 1

To a solution of (3-methoxyphenyl)-(3-pyridinyl) methanone (500 mg) in THF (10 ml) was added 1.1M cyclopropylmagnesium bromide THF solution (2 ml) at 0° C. The reaction mixture was warmed to room temperature, and stirred for 30 minutes. Aqueous ammonium chloride and ethyl acetate were added to the reaction mixture, the organic layer was separated and washed with saturated aqueous sodium chloride, and dried with magnesium sulfate. The solvent was distilled off under reduced pressure. The residue was filtered and washed with ethyl acetate-hexane (1:2) to give cyclopropyl-(3-methoxyphenyl)-(3-pyridinyl)methanol (470 mg).

$^1$H-NMR (CDCl$_3$) δ: 0.45–0.59(4H,m), 1.48–1.61(1H, m), 3.65(1H,brs), 3.71(3H,s), 6.78(1H,dd), 6.92–7.22(4H, m), 7.69(1H,dd), 8.27(1H,dd), 8.55(1H,d).

Step 2

To a solution of the product of step 1 (470 mg) in acetic acid (5 ml) was added 48% aqueous HBr (3 ml) at 10° C. The reaction mixture was warmed to room temperature, and stirred for 12 hours. Water and ethyl acetate were added to the reaction mixture and neutralized with dilute NaOH solution. The organic layer was separated and washed with saturated aqueous sodium chloride, and dried over magnesium sulfate. The solvent was distilled off under reduced pressure. The residue was purified by silica gel chromatography eluting with ethyl acetate-hexane (1:4) to give 4-bromo-1-(3-methoxyphenyl)-1-(3-pyridinyl)-1-butene (560 mg).

$^1$H-NMR (CDCl$_3$) δ: 2.66–2.74(2H,m), 3.41–3.46(2H, m), 3.67(0.6×3H,s), 3.79(0.4×3H,s), 6.15–6.18(1H,m), 6.73–6.80(3H,m), 7.17–7.47(3H,m), 8.46–8.64(2H,m).

Step 3

To a solution the product of step 2 (500 mg) in DMF (20 ml) were added 4-(4-chlorophenyl)-4-hydroxypiperidine (500 mg), potassium carbonate (430 mg), potassium iodide (130 mg) and the mixture was stirred at room temperature for 12 hours. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with methylene chloride-methanol (10:1) to give the titled compound as major regioisomer (225 mg) and minor one (140 mg)

Major Isomer $^1$H-NMR (CDCl$_3$) δ: 1.65–1.78(2H,m), 1.98–2.83(11H, m), 3.79(3H,s), 6.22(1H,t), 6.75–6.84(4H,m), 7.18–7.57 (6H,m), 8.42(1H,d), 8.50(1H,dd). MS m/z: 449 (M+1).

Minor Isomer $^1$H-NMR (CDCl$_3$) δ: 1.65–1.79(2H,m), 2.08–2.88(11H, m), 3.79(3H,s), 6.12(1H,t), 6.68–6.94(4H,m), 7.15–7.53 (6H,m), 8.40(1H,dd) , 8.53(1H,d) MS m/z: 449 (M+1).

Example 2

4-(4-Chlorophenyl)-1-[4-phenyl-4-(3-pyridinyl)-3-butenyl]piperidin-4-ol

The titled compound was prepared by following the procedure of example 1, but replacing (3-methoxyphenyl)-(3-pyridinyl)methanone with phenyl-(3-pyridinyl) methanone.

Major Isomer $^1$H-NMR (CDCl$_3$) δ: 1.67–1.72 (2H,m) , 2.07–2.19(3H, m) , 2.31–2.61(6H,m), 2.75–2.80(2H,m), 6.18(1H,t), 7.16–7.48(11H, m) , 8.44 (1H,d) , 8.49(1H,dd) MS m/z: 419 (M+1).

Minor Isomer $^1$H-NMR (CDCl$_3$) δ: 1.69–1.74(2H,m) , 2.18–2.23(3H, m), 2.43–2.66(6H,m), 2.82–2.86(2H,m), 6.18(1H,t), 7.16–7.48(11H,m), 8.44(1H,dd), 8.51(1H,d). MS m/z: 419 (M+1).

Example 3

4-(4-Chlorophenyl)-1-[4-(2,5-dimethoxyphenyl)-4-(3-pyridinyl)-3-butenyl]piperidin-4-ol The titled compound was prepared by following the procedure of example 1, but replacing (3-methoxyphenyl)-(3-pyridinyl)methanone with (2,5-dimethoxyphenyl)-(3-pyridinyl)methanone.

Major Isomer $^1$H-NMR (CDCl$_3$) δ: 1.62–1.79(2H,m), 1.97–2.18(2H, m), 2.32–2.81(9H,m) 3.47(3H,s), 3.79(3H,s), 5.92(1H,t), 6.68–6.82(3H,m), 7.11–7.49(6H,m), 8.35(1H,dd), 8.41(1H, d). MS m/z: 479 (M+1).

13

Minor Isomer $^1$H-NMR (CDCl$_3$) δ: 1.62–1.79(2H,m), 2.01–2.20(2H, m), 2.28–2.81(9H,m) 3.49(3H,s), 3.80(3H,s), 5.91(1H,t), 6.70–6.84(3H,m), 7.12–7.50(6H,m), 8.35(1H,dd), 8.41(1H, d). MS m/z: 479 (M+1)

Example 4

1-[4-(2-Bromo-4-pyridinyl)-4-(3-pyridinyl)-3-butenyl]-4-(4-chlorophenyl)piperidin-4-ol The titled compound was prepared by following the procedure of example 1, but replacing (3-methoxyphenyl)-(3-pyridinyl)methanone with (2-bromo-4-pyridinyl)-(3-pyridinyl)methanone.

$^1$H-NMR (CDCl$_3$) δ: 1.65–1.70(2H,m), 1.92–2.18(5H, m), 2.38–2.54(4H,m), 2.67–2.72(2H,m), 6.31(1H,t), 7.14–7.41(7H,m), 8.38–8.41(2H,m), 8.52(1H,d), 8.75(1H, s). MS m/z: 500 (M+1).

Examples 5–90 can be prepared by the schemes set forth is FIGS. 1–5 and the procedures described above.

Example 91

Membrane Preparations for Chemokine Binding and Binding Assays

Membranes were prepared from THP-1 cells (ATCC #TIB202). Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 μg/ml each aprotinin, leupeptin, and chymostatin (protease inhibitors), and 100 μg/ml PMSF (phenyl methane sulfonyl fluoride—also a protease inhibitor), at a concentration of 1 to 5×10$^7$ cells/ml. This procedure results in cell lysis. The suspension was mixed well to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 μg/ml each aprotinin, leupeptin, and chymostatin, and 10 μg/ml PMSF (approximately 0.1 ml per each 10$^8$ cells) . All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays—utilized the membranes described above. Membrane protein (2 to 20 μg total membrane protein) was incubated with 0.1 to 0.2 nM $^{125}$I-labeled RANTES or MIP-1α with or without unlabeled competitor (RANTES or MIP-1α) or various concentrations of compounds. The binding reactions were performed in 60 to 100 μl of a binding buffer consisting of 10 mM HEPES pH 7.2, 1 mM CaCl$_2$, 5 mM MgCl$_2$, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 μl of binding buffer containing 0.5 M NaCl, dried, and the amount of bound radioactivity was determined by scintillation counting in a Topcount beta-plate counter.

14

The activities of test compounds are reported in the Table below as IC$_{50}$ values or the inhibitor concentration required for 50% inhibition of specific binding in receptor binding assays using $^{125}$I-RANTES or $^{125}$MIP-1α as ligand and THP-1 cell membranes. Specific binding is defined as the total binding minus the non-specific binding; non-specific binding is the amount of cpm still detected in the presence of excess unlabeled Rantes or $^{125}$MIP-1α.

TABLE

| BIOLOGICAL DATA | |
|---|---|
| Example | IC$_{50}$ (μM) |
| 1 | <1 |
| 2 | <1 |
| 3 | <1 |
| 4 | >1 |

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A method of treating a disease associated with aberrant leukocyte recruitment and/or activation mediated by chemokine receptor function comprising administering to a subject in need thereof an effective amount of a compound represented by the following structural formula:

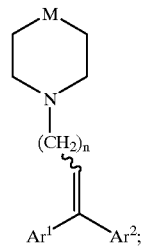

or physiologically acceptable salt thereof, wherein:

Ar$^1$ is a substituted or unsubstituted pyridyl group;

Ar$^2$ is a substituted or unsubstituted aromatic carbocyclic or group;

n is an integer from one to four;

M is >CR$^1$R$^2$;

R$^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$;

R$^2$ is —OH, an acyl group, a substituted acyl group, —NR$^5$R$^6$, a substituted or unsubstituted C$_2$–C$_{20}$ linear alkyl, alkenyl or alkynyl group, a substituted or unsubstituted C$_3$–C$_{20}$ branched alkyl or alkenyl group, a substituted or unsubstituted C$_4$–C$_{20}$ branched alkynyl group, a substituted or unsubstituted C$_3$–C$_{20}$ cyclic alkyl or alkenyl group, a substituted or unsubstituted C$_9$–C$_{20}$ cyclic alkynyl group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl; and $R^3$, $R^4$, $R^5$ and $R^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or $R^1$ and $R^2$, $R^3$ and $R^4$, or $R^5$ and $R^6$ taken together with the atom to which they are bonded, form a substituted or unsubstituted non-aromatic heterocyclic ring.

2. The method of claim 1 wherein:

$Ar^1$ or $Ar^2$ is substituted with —OH, a halogen, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$; wherein:

u is zero or one;

t is an integer from zero to three;

$R^{20}$, $R^{21}$ or $R^{22}$ are independently —H, an aliphatic group, a substituted aliphatic group, an aromatic group, a substituted aromatic group or a non-aromatic heterocyclic group; or $R^{21}$ and $R^{22}$, taken together with the nitrogen atom to which they are bonded, form a non-aromatic heterocyclic ring.

3. The method of claim 1 wherein $R^1$ is —H or —OH.

4. The method of claim 1 wherein $R^2$ is a substituted or unsubstituted aromatic group.

5. The method of claim 1 wherein:

$Ar^1$ is a substituted or unsubstituted 3-pyridyl group.

6. The method of claim 5 wherein:

$Ar^1$ or $Ar^2$ is substituted with —OH, a halogen, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$; wherein:

u is zero or one;

t is an integer from zero to three;

$R^{20}$, $R^{21}$ or $R^{22}$ are independently —H, an aliphatic group, a substituted aliphatic group, an aromatic group, a substituted aromatic group or a non-aromatic heterocyclic group; or $R^{21}$ and $R^{22}$, taken together with the nitrogen atom to which they are bonded, form a non-aromatic heterocyclic ring.

7. The method of claim 5 wherein $Ar^2$ is a substituted or unsubstituted phenyl group.

8. The method of claim 7 wherein said phenyl group is substituted with —OH, a halogen, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$; wherein:

u is zero or one;

t is an integer from zero to three;

$R^{20}$, $R^{21}$ or $R^{22}$ are independently —H, an aliphatic group, a substituted aliphatic group, an aromatic group, a substituted aromatic group or a non-aromatic heterocyclic group; or $R^{21}$ and $R^{22}$, taken together with the nitrogen atom to which they are bonded, form a non-aromatic heterocyclic ring.

9. A method of treating a disease associated with aberrant leukocyte recruitment and/or activation mediated by chemokine receptor function comprising administering to a subject in need thereof an effective amount of a compound represented by the following structural formula:

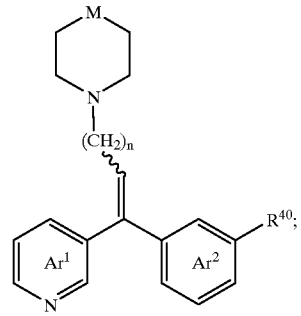

or physiologically acceptable salt thereof, wherein:

n is an integer from one to four;

M is >CR$^1$R$^2$;

$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$;

$R^2$ is —OH, an acyl group, a substituted acyl group, —NR$^5$R$^6$, a substituted or unsubstituted C$_2$–C$_{20}$ linear alkyl, alkenyl or alkynyl group, a substituted or unsubstituted C$_3$–C$_{20}$ branched alkyl or alkenyl group, a substituted or unsubstituted C$_4$–C$_{20}$ branched alkynyl group, a substituted or unsubstituted C$_3$–C$_{20}$ cyclic alkyl or alkenyl group, a substituted or unsubstituted C$_9$–C$_{20}$ cyclic alkynyl group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl;

$R^3$, $R^4$, $R^5$ and $R^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or $R^1$ and $R^2$, $R^3$ and $R^4$, or $R^5$ and $R^6$ taken together with the atom to which they are bonded, form a substituted or unsubstituted non-aromatic heterocyclic ring; and $R^{40}$ is —OH, halogen, aliphatic group, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$; wherein:

u is zero or one;

t is an integer from zero to three;

$R^{20}$, $R^{21}$ or $R^{22}$ are independently —H, an aliphatic group, a substituted aliphatic group, an aromatic group, a substituted aromatic group or a non-aromatic heterocyclic group; or $R^{21}$ and $R^{22}$, taken together with the nitrogen atom to which they are bonded, form a non-aromatic heterocyclic ring.

10. The method of claim 9 wherein $R^{40}$ is —O-alkyl.

11. The method of claim 9 wherein:
$R^1$ is —H or —OH;
$R^2$ is a substituted or unsubstituted aromatic group; and
n is two.

12. The method of claim 11 wherein $R^{40}$ is —O—$CH_3$.

13. A compound represented by the following structural formula:

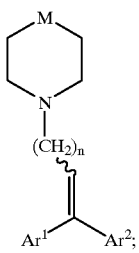

or physiologically acceptable salt thereof, wherein:
$Ar^1$ is a substituted or unsubstituted pyridyl group;
$Ar^2$ is a substituted or unsubstituted aromatic carbocyclic;
n is an integer from one to four;
M is >$CR^1R^2$;
$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—$NR^3R^4$ or —$NR^3R^4$;
$R^2$ is —OH, an acyl group, a substituted acyl group, —$NR^5R^6$, a substituted or unsubstituted $C_2$–$C_{20}$ linear alkyl, alkenyl or alkynyl group, a substituted or unsubstituted $C_3$–$C_{20}$ branched alkyl or alkenyl group, a substituted or unsubstituted $C_4$–$C_{20}$ branched alkynyl group, a substituted or unsubstituted $C_3$–$C_{20}$ cyclic alkyl or alkenyl group, a substituted or unsubstituted $C_9$–$C_{20}$ cyclic alkynyl group, an aromatic group, a substituted aromatic group, a benzyl group, a substituted benzyl group; wherein:
said acyl group is an aliphatic carbonyl, aromatic carbonyl, aliphatic sulfonyl or aromatic sulfonyl; and
$R^3$, $R^4$, $R^5$ and $R^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or
$R^1$ and $R^2$, $R^3$ and $R^4$, or $R^5$ and $R^6$ taken together with the atom to which they are bonded, form a substituted or unsubstituted non-aromatic heterocyclic ring.

14. The compound of claim 13 wherein:
$Ar^1$ or $Ar^2$ is substituted with —OH, a halogen, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$;
wherein:
u is zero or one;
t is an integer from zero to three;
$R^{20}$, $R^{21}$ or $R^{22}$ are independently —H, an aliphatic group, a substituted aliphatic group, an aromatic group, a substituted aromatic group or a non-aromatic heterocyclic group; or
$R^{21}$ and $R^{22}$, taken together with the nitrogen atom to which they are bonded, form a non-aromatic heterocyclic ring.

15. The compound of claim 13 wherein $R^1$ is —H or —OH.

16. The compound of claim 13 wherein $R^2$ is a substituted or unsubstituted aromatic group.

17. The compound of claim 13 wherein:
$Ar^1$ is a substituted or unsubstituted 3-pyridyl group.

18. The compound of claim 17 wherein:
$Ar^1$ or $Ar^2$ is substituted with —OH, a halogen, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$;
wherein:
u is zero or one;
t is an integer from zero to three;
$R^{20}$, $R^{21}$ or $R^{22}$ are independently —H, an aliphatic group, a substituted aliphatic group, an aromatic group, a substituted aromatic group or a non-aromatic heterocyclic group; or
$R^{21}$ and $R^{22}$, taken together with the nitrogen atom to which they are bonded, form a non-aromatic heterocyclic ring.

19. The compound of claim 17 wherein $Ar^2$ is a substituted or unsubstituted phenyl group.

20. The compound of claim 19 wherein said phenyl group is substituted with —OH, a halogen, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$;
wherein:
u is zero or one;
t is an integer from zero to three;
$R^{20}$, $R^{21}$ or $R^{22}$ are independently —H, an aliphatic group, a substituted aliphatic group, an aromatic group, a substituted aromatic group or a non-aromatic heterocyclic group; or
$R^{21}$ and $R^{22}$, taken together with the nitrogen atom to which they are bonded, form a non-aromatic heterocyclic ring.

21. A compound represented by the following structural formula:

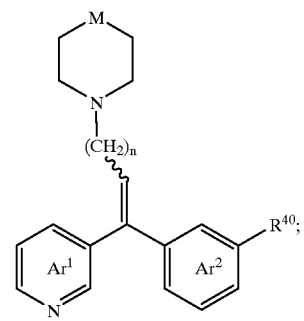

or physiologically acceptable salt thereof, wherein:
n is an integer from one to four;
M is >$CR^1R^2$;
$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—$NR^3R^4$ or —$NR^3R^4$;
$R^2$ is —OH, an acyl group, a substituted acyl group, —$NR^5R^6$, a substituted or unsubstituted $C_2$–$C_{20}$ linear alkyl, alkenyl or alkynyl group, a substituted or unsubstituted $C_3$–$C_{20}$ branched alkyl or alkenyl group, a substituted or unsubstituted $C_4$–$C_{20}$ branched alkynyl group, a substituted or unsubstituted $C_3$–$C_{20}$ cyclic alkyl or alkenyl group, a substituted or unsubstituted $C_9$–$C_{20}$ cyclic alkynyl group, an aromatic group, a substituted aromatic group, a benzyl group, a substituted benzyl group, a non-aromatic heterocyclic group or a substituted non-aromatic heterocyclic group; wherein:

$R^3$, $R^4$, $R^5$ and $R^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or $R^1$ and $R^2$, $R^3$ and $R^4$, or $R^5$ and $R^6$ taken together with the atom to which they are bonded, form a substituted or unsubstituted non-aromatic heterocyclic ring;

said acyl group is an aliphatic carbonyl, aromatic carbonyl, aliphatic sulfonyl or aromatic sulfonyl; and $R^{40}$ is —OH, halogen, aliphatic group, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$; wherein:

u is zero or one;

t is an integer from zero to three;

$R^{20}$, $R^{21}$ or $R^{22}$ are independently —H, an aliphatic group, a substituted aliphatic group, an aromatic group, a substituted aromatic group or a non-aromatic heterocyclic group; or $R^{21}$ and $R^{22}$, taken together with the nitrogen atom to which they are bonded, form a non-aromatic heterocyclic ring.

22. The compound of claim 21 wherein $R^{40}$ is —O-alkyl.

23. The compound of claim 21 wherein:

$R^1$ is —H or —OH;

$R^2$ is a substituted or unsubstituted aromatic group; and n is two.

24. The compound of claim 23 wherein $R^{40}$ is —O—CH$_3$.

25. A method of antagonizing a chemokine receptor in a mammal in need thereof comprising administering to said mammal a chemokine receptor antagonizing amount of a compound represented by:

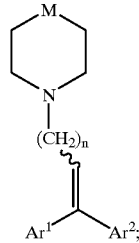

or physiologically acceptable salt thereof, wherein:

Ar$^1$ is a substituted or unsubstituted pyridyl group;

Ar$^2$ is a substituted or unsubstituted aromatic carbocyclic group;

n is an integer from one to four;

M is >CR$^1$R$^2$;

$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$; and $R^2$ is —H, —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl aromatic carbonyl, aliphatic sulfonyl or aromatic sulfonyl;

$R^3$, $R^4$, $R^5$ and $R^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or $R^1$ and $R^2$, $R^3$ and $R^4$, or $R^5$ and $R^6$ taken together with the atom to which they are bonded, form a substituted or unsubstituted non-aromatic heterocyclic ring.

26. A method of treating a disease associated with aberrant leukocyte recruitment and/or activation mediated by chemokine receptor function, said disease being selected from the group consisting of arthritis, psoriasis, multiple sclerosis, rejection of a transplanted organ or tissue, graft versus host disease, ulcerative colitis, Crohn's disease, allergy, asthma, AIDS associated encephalitis, AIDS related maculopapular skin eruption, AIDS related interstitial pneumonia, AIDS related enteropathy, AIDS related periportal hepatic inflammation and AIDS related glomerulo nephritis, comprising administering to a subject in need thereof an effective amount of a compound represented by the following structural formula:

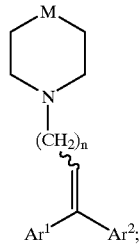

or physiologically acceptable salt thereof, wherein:

Ar$^1$ is a substituted or unsubstituted pyridyl group;

Ar$^2$ is a substituted or unsubstituted aromatic carbocyclic group;

n is an integer from one to four;

M is >CR$^1$R$^2$;

$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$;

$R^2$ is —OH, an acyl group, a substituted acyl group, —NR$^5$R$^6$, a substituted or unsubstituted $C_2$–$C_{20}$ linear alkyl, alkenyl or alkynyl group, a substituted or unsubstituted $C_3$–$C_{20}$ branched alkyl or alkenyl group a substituted or unsubstituted $C_4$–$C_{20}$ branched alkynyl group a substituted or unsubstituted $C_3$–$C_{20}$ cyclic alkyl or alkenyl group, a substituted or unsubstituted $C_9$–$C_{20}$ cyclic alkynyl group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl; and R³, R⁴, R⁵ and R⁶ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or R¹ and R², R³ and R⁴, or R⁵ and R⁶ taken together with the atom to which they are bonded, form a substituted or unsubstituted non-aromatic heterocyclic ring.

27. The method of claim 25 wherein Ar² is a substituted or unsubstituted phenyl group.

28. The method of claim 25 wherein R¹ is —H or —OH.

29. The method of claim 25 wherein R² is a substituted or unsubstituted aromatic group.

30. The method of claim 25 wherein:
Ar¹ is a substituted or unsubstituted 3-pyridyl group.

31. A method of antagonizing a chemokine receptor in a mammal in need thereof, comprising administering to said mammal an effective amount of a compound represented by:

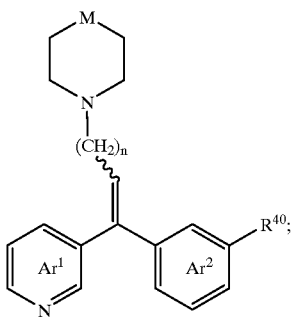

or physiologically acceptable salt thereof, wherein:
n is an integer from one to four;
M is >CR¹R²;
R¹ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR³R⁴ or —NR³R⁴; and R² is —H, —OH, an acyl group, a substituted acyl group, —NR⁵R⁶, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl;

R³, R⁴, R⁵ and R⁶ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or R¹ and R², R³ and R⁴, or R⁵ and R⁶ taken together with the atom to which they are bonded, form a substituted or unsubstituted non-aromatic heterocyclic ring; and R⁴⁰ is —OH, halogen, aliphatic group, —O-(aliphatic group), —O-(substituted aliphatic group), —O-(aromatic group), —O-(substituted aromatic group), an electron withdrawing group, —(O)ᵤ—(CH₂)ₜ—COOR²⁰, —(O)ᵤ—(CH₂)ₜ—C(O)—NR²¹R²² or —(O)ᵤ—(CH₂)ₜ—NHC(O)—O—R²⁰; wherein:
u is zero or one;
t is an integer from zero to three;
R²⁰, R²¹ or R²² are independently —H, an aliphatic group, a substituted aliphatic group, an aromatic group, a substituted aromatic group or a non-aromatic heterocyclic group; or R²¹ and R²², taken together with the nitrogen atom to which they are bonded, form a non-aromatic heterocyclic ring.

32. The method of claim 31 wherein R⁴⁰ is —O-alkyl.

33. The method of claim 31 wherein R⁴⁰ is —(O)ᵤ—(CH₂)ₜ—COOR²⁰, wherein u is zero, t is zero and R²⁰ is —H.

34. The method of claim 31 wherein:
R¹ is —H or —OH; and
R² is a substituted or unsubstituted aromatic group.

35. A compound represented by the following structural formula:

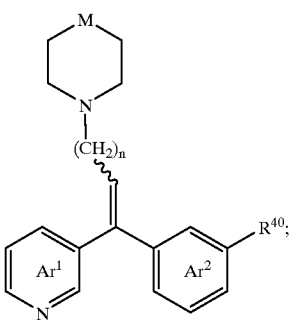

or physiologically acceptable salt thereof, wherein:
n is an integer from one to four;
M is >CR¹R²;
R¹ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR³R⁴ or —NR³R⁴;

R² is —OH, an acyl group, a substituted acyl group, —NR⁵R⁶, a substituted or unsubstituted C₂–C₂₀ linear alkyl, alkenyl or alkynyl group, a substituted or unsubstituted C₃–C₂₀ branched alkyl or alkenyl group, a substituted or unsubstituted C₄–C₂₀ branched alkynyl group, a substituted or unsubstituted C₃–C₂₀ cyclic alkyl or alkenyl group, a substituted or unsubstituted C₉–C₂₀ cyclic alkynyl group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl;

R³, R⁴, R⁵ and R⁶ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or R¹ and R², R³ and R⁴, or R⁵ and R⁶ taken together with the atom to which they are bonded, form a substituted or unsubstituted non-aromatic heterocyclic ring;

R⁴⁰ is —(O)ᵤ—(CH₂)ₜ—COOR²⁰; wherein:
u is zero;
t is zero; and
R²⁰ is —H.

36. A compound represented by the following structural formula:

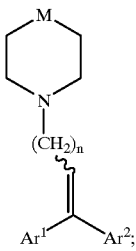

or physiologically acceptable salt thereof, wherein:

Ar$^1$ is a substituted or unsubstituted pyridyl group;

Ar$^2$ is a substituted or unsubstituted aromatic carbocyclic group;

n is an integer from one to four;

M is >CR$^1$R$^2$;

R$^1$ is —H or —OH;

R$^2$ is phenyl, substituted phenyl, pyridyl, substituted pyridyl, napthyl, substituted napthyl, quinolinyl, substituted quinolinyl, anthracyl, substituted anthracyl, benzyl or substituted benzyl; or R$^1$ and R$^2$ taken together with the atom to which they are bonded, form a substituted or unsubstituted non-aromatic heterocyclic ring.

37. A compound represented by the following structural formula:

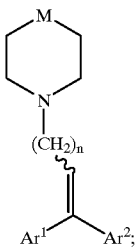

or physiologically acceptable salt thereof, wherein:

Ar$^1$ is a substituted or unsubstituted pyridyl group;

Ar$^2$ is a substituted or unsubstituted aromatic carbocyclic group;

n is an integer from one to four;

M is >CR$^1$R$^2$;

R$^1$ is —H or —OH; and

R$^2$ is a substituted or unsubstituted non-aromatic heterocyclic group, wherein said non-aromatic heterocyclic group is tetrahydrofuranyl, tetrahyrothiophenyl, morpholino, thiomorpholino, pyrrolidinyl, piperazinyl, piperidinyl, thiazolidinyl, diazolonyl, phthalimidyl, benzoxanyl, benzopyrolidinyl, benzopiperidinyl, benzoxolanyl, benzothiolanyl and benzothianyl.

38. A method of treating a disease mediated by chemokine receptor function, comprising administering to a subject in need thereof an effective amount of a compound represented by the following structural formula:

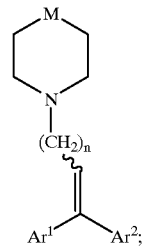

or physiologically acceptable salt thereof, wherein:

Ar$^1$ is a substituted or unsubstituted pyridyl group;

Ar$^2$ is a substituted or unsubstituted aromatic carbocyclic group;

n is an integer from one to four;

M is >CR$^1$R$^2$;

R$^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$;

R$^2$ is —H, —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl; and R$^3$, R$^4$, R$^5$ and R$^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or R$^1$ and R$^2$, R$^3$ and R$^4$, or R$^5$ and R$^6$ taken together with the atom to which they are bonded, form a substituted or unsubstituted non-aromatic heterocyclic ring.

39. A method of treating a disease associated with aberrant leukocyte recruitment and/or activation mediated by chemokine receptor function comprising administering to a subject in need thereof an effective amount of a compound represented by the following structural formula:

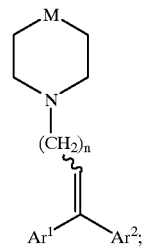

or physiologically acceptable salt thereof, wherein:

Ar$^1$ is a substituted or unsubstituted pyridyl group;

Ar$^2$ is a substituted or unsubstituted aromatic carbocyclic or group;

n is an integer from one to four;

M is >CR$^1$R$^2$;

R$^1$ is —H, —OH, an aliphatic group, —O-(aliphatic group), —O-(substituted aliphatic group), —SH, —S-

(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$;

R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl; and R$^3$, R$^4$, R$^5$ and R$^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or R$^1$ and R$^2$, R$^3$ and R$^4$, or R$^5$ and R$^6$ taken together with the atom to which they are bonded, form a substituted or unsubstituted non-aromatic heterocyclic ring;

with the proviso that when R$^1$ is —H, R$^2$ is not methyl.

40. A method of treating a disease associated with aberrant leukocyte recruitment and/or activation mediated chemokine receptor function comprising administering to a subject in need thereof an effective amount of a compound represented by the following structural formula:

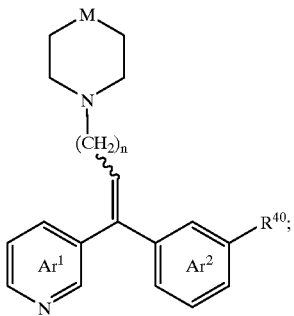

or physiologically acceptable salt thereof, wherein:

n is an integer from one to four;

M is >CR$^1$R$^2$;

R$^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$; and R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl;

R$^3$, R$^4$, R$^5$ and R$^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or R$^1$ and R$^2$, R$^3$ and R$^4$, or R$^5$ and R$^6$ taken together with the atom to which they are bonded, form a substituted or unsubstituted non-aromatic heterocyclic ring; and R$^{40}$ is —OH, halogen, aliphatic group, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$; wherein:

u is zero or one;

t is an integer from zero to three;

R$^{20}$, R$^{21}$ or R$^{22}$ are independently —H, an aliphatic group, a substituted aliphatic group, an aromatic group, a substituted aromatic group or a non-aromatic heterocyclic group; or R$^{21}$ and R$^{22}$, taken together with the nitrogen atom to which they are bonded, form a non-aromatic heterocyclic ring;

with the proviso that when R$^1$ is —H, R$^2$ is not methyl.

41. A compound represented by the following structural formula:

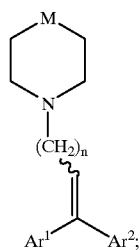

or physiologically acceptable salt thereof, wherein:

Ar$^1$ is a substituted or unsubstituted pyridyl group;

Ar$^2$ is a substituted or unsubstituted aromatic carbocyclic;

n is an integer from one to four;

M is >CR$^1$R$^2$;

R$^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$; and R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group; wherein:

said acyl group is an aliphatic carbonyl, aromatic carbonyl, aliphatic sulfonyl or aromatic sulfonyl;

R$^3$, R$^4$, R$^5$ and R$^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or R$^1$ and R$^2$, R$^3$ and R$^4$, or R$^5$ and R$^6$ taken together with the atom to which they are bonded, form a substituted or unsubstituted non-aromatic heterocyclic ring;

with the proviso that when R$^1$ is —H, R$^2$ is not methyl.

42. A compound represented by the following structural formula:

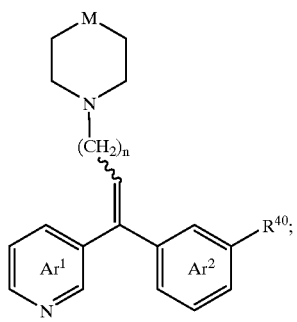

or physiologically acceptable salt thereof, wherein:
  n is an integer from one to four;
  M is >CR$^1$R$^2$;
  R$^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$; and
  R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:
  R$^3$, R$^4$, R$^5$ and R$^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or
  R$^1$ and R$^2$, R$^3$ and R$^4$, or R$^5$ and R$^6$ taken together with the atom to which they are bonded, form a substituted or unsubstituted non-aromatic heterocyclic ring;
  said acyl group is an aliphatic carbonyl, aromatic carbonyl, aliphatic sulfonyl or aromatic sulfonyl; and
  R$^{40}$ is —OH, halogen, aliphatic group, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$; wherein:
  u is zero or one;
  t is an integer from zero to three;
  R$^{20}$, R$^{21}$ or R$^{22}$ are independently —H, an aliphatic group, a substituted aliphatic group, an aromatic group, a substituted aromatic group or a non-aromatic heterocyclic group; or
  R$^{21}$ and R$^{22}$, taken together with the nitrogen atom to which they are bonded, form a non-aromatic heterocyclic ring;
  with the proviso that when R$^1$ is —H, R$^2$ is not methyl.

43. A method of treating a disease associated with aberrant leukocyte recruitment and/or activation mediated by chemokine receptor function, said disease being selected from the group consisting of arthritis, psoriasis, multiple sclerosis, rejection of a transplanted organ or tissue, graft versus host disease, ulcerative colitis, Crohn's disease, allergy, asthma, AIDS associated encephalitis, AIDS related maculopapular skin eruption, AIDS related interstitial pneumonia, AIDS related enteropathy, AIDS related periportal hepatic inflammation and AIDS related glomerulonephritis, comprising administering to a subject in need thereof an effective amount of a compound represented by the following structural formula:

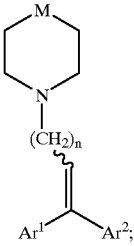

or physiologically acceptable salt thereof, wherein:
  Ar$^1$ is a substituted or unsubstituted pyridyl group;
  Ar$^2$ is a substituted or unsubstituted aromatic carbocyclic group;
  n is an integer from one to four;
  M is >CR$^1$R$^2$;
  R$^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$;
  R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:
  said acyl group is an aliphatic carbonyl, aromatic carbonyl, aliphatic sulfonyl or aromatic sulfonyl; and
  R$^3$, R$^4$, R$^5$ and R$^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or
  R$^1$ and R$^2$, R$^3$ and R$^4$, or R$^5$ and R$^6$ taken together with the atom to which they are bonded, form a substituted or unsubstituted non-aromatic heterocyclic ring;
  with the proviso that when R$^1$ is —H, R$^2$ is not methyl.

44. A compound represented by the following structural formula:

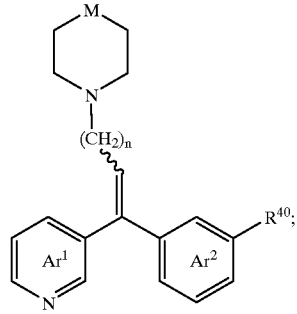

or physiologically acceptable salt thereof, wherein:
  n is an integer from one to four;
  M is >CR$^1$R$^2$;
  R$^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —CN, —COOH, —CO—NR$^3$R$^4$ or —NR$^3$R$^4$; and $R^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

said acyl group is an aliphatic carbonyl, aromatic carbonyl, aliphatic sulfonyl or aromatic sulfonyl;

$R^3$, $R^4$, $R^5$ and $R^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or $R^1$ and $R^2$, $R^3$ and $R^4$, or $R^5$ and $R^6$ taken together with the atom to which they are bonded, form a substituted or unsubstituted non-aromatic heterocyclic ring;

$R^{40}$ is —(O)$_u$—(CH$_2$)$_t$—COOR$^{20}$; wherein:

u is zero;

t is zero; and $R^{20}$ is —H;

with the proviso that when $R^1$ is —H, $R^2$ is not methyl.

* * * * *